US009636016B1

(12) United States Patent
Etzkorn et al.

(10) Patent No.: US 9,636,016 B1
(45) Date of Patent: *May 2, 2017

(54) EYE-MOUNTABLE DEVICES AND METHODS FOR ACCURATELY PLACING A FLEXIBLE RING CONTAINING ELECTRONICS IN EYE-MOUNTABLE DEVICES

(71) Applicant: Verily Life Sciences LLC, Mountain View, CA (US)

(72) Inventors: James Etzkorn, Mountain View, CA (US); Harvey Ho, Mountain View, CA (US); Jeffrey George Linhardt, Pleasanton, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 1075 days.

This patent is subject to a terminal disclaimer.

(21) Appl. No.: 13/750,782

(22) Filed: Jan. 25, 2013

(51) Int. Cl.
*B29D 11/00* (2006.01)
*A61B 5/00* (2006.01)
*G02C 7/04* (2006.01)

(52) U.S. Cl.
CPC .......... *A61B 5/00* (2013.01); *B29D 11/00038* (2013.01); *B29D 11/00807* (2013.01); *G02C 7/04* (2013.01)

(58) Field of Classification Search
CPC ............ A61B 5/6821; B29D 11/00038; B29D 11/00807; G02C 7/04
See application file for complete search history.

(56) References Cited

U.S. PATENT DOCUMENTS 3,958,560 A 5/1976 March
4,014,321 A 3/1977 March
(Continued)

FOREIGN PATENT DOCUMENTS

EP 0369942 5/1990
EP 0686372 12/1995
(Continued)

OTHER PUBLICATIONS

Badugu et al., "A Glucose Sensing Contact Lens: A Non-Invasive Technique for Continuous Physiological Glucose Monitoring," Journal of Fluorescence, Sep. 2003, pp. 371-374, vol. 13, No. 5.
(Continued)

*Primary Examiner* — Binh X Tran
(74) *Attorney, Agent, or Firm* — McDonnell Boehnen Hulbert & Berghoff LLP

(57) ABSTRACT

Example eye-mountable devices and methods for placing a flexible ring containing electronics in an eye-mountable device are described. A method may involve forming a first polymer layer, which defines a posterior side of an eye-mountable device. Further, the method may involve positioning a ring-shaped structure on the first polymer layer in a predetermined rotational orientation, wherein the ring-shaped structure comprises a sensor configured to detect an analyte. Still further, the method may involve forming a second polymer layer over the first polymer layer and the ring-shaped structure, such that the ring-shaped structure is fully enclosed by the first polymer layer and the second polymer layer. The second polymer layer defines an anterior side of the eye-mountable device. The method may also involve forming a channel through the second polymer layer based on the predetermined rotational orientation, such that the sensor is configured to receive the analyte via the channel.

18 Claims, 15 Drawing Sheets

(56) References Cited

U.S. PATENT DOCUMENTS

| | | |
|---|---|---|
| 4,055,378 A | 10/1977 | Feneberg et al. |
| 4,122,942 A | 10/1978 | Wolfson |
| 4,136,250 A | 1/1979 | Mueller et al. |
| 4,143,949 A | 3/1979 | Chen |
| 4,153,641 A | 5/1979 | Deichert et al. |
| 4,214,014 A | 7/1980 | Hofer et al. |
| 4,309,085 A | 1/1982 | Morrison |
| 4,312,575 A | 1/1982 | Peyman et al. |
| 4,401,371 A | 8/1983 | Neefe |
| 4,463,149 A | 7/1984 | Ellis |
| 4,555,372 A | 11/1985 | Kunzler et al. |
| 4,604,479 A | 8/1986 | Ellis |
| 4,632,844 A | 12/1986 | Yanagihara et al. |
| 4,686,267 A | 8/1987 | Ellis et al. |
| 4,740,533 A | 4/1988 | Su et al. |
| 4,826,936 A | 5/1989 | Ellis |
| 4,996,275 A | 2/1991 | Ellis et al. |
| 4,997,770 A | 3/1991 | Giles et al. |
| 5,032,658 A | 7/1991 | Baron et al. |
| 5,034,461 A | 7/1991 | Lai et al. |
| 5,070,215 A | 12/1991 | Bambury et al. |
| 5,135,297 A | 8/1992 | Valint et al. |
| 5,177,165 A | 1/1993 | Valint et al. |
| 5,177,168 A | 1/1993 | Baron et al. |
| 5,219,965 A | 6/1993 | Valint et al. |
| 5,260,000 A | 11/1993 | Nandu et al. |
| 5,271,875 A | 12/1993 | Appleton et al. |
| 5,310,779 A | 5/1994 | Lai |
| 5,321,108 A | 6/1994 | Kunzler et al. |
| 5,326,584 A | 7/1994 | Kamel et al. |
| 5,336,797 A | 8/1994 | McGee et al. |
| 5,346,976 A | 9/1994 | Ellis et al. |
| 5,358,995 A | 10/1994 | Lai et al. |
| 5,364,918 A | 11/1994 | Valint et al. |
| 5,387,662 A | 2/1995 | Kunzler et al. |
| 5,449,729 A | 9/1995 | Lai |
| 5,472,436 A | 12/1995 | Fremstad |
| 5,512,205 A | 4/1996 | Lai |
| 5,585,871 A | 12/1996 | Linden |
| 5,610,252 A | 3/1997 | Bambury et al. |
| 5,616,757 A | 4/1997 | Bambury et al. |
| 5,682,210 A | 10/1997 | Weirich |
| 5,708,094 A | 1/1998 | Lai et al. |
| 5,710,302 A | 1/1998 | Kunzler et al. |
| 5,714,557 A | 2/1998 | Kunzler et al. |
| 5,726,733 A | 3/1998 | Lai et al. |
| 5,760,100 A | 6/1998 | Nicolson et al. |
| 5,908,906 A | 6/1999 | Kunzler et al. |
| 5,981,669 A | 11/1999 | Valint et al. |
| 6,087,941 A | 7/2000 | Ferraz et al. |
| 6,131,580 A | 10/2000 | Ratner et al. |
| 6,193,369 B1 | 2/2001 | Valint et al. |
| 6,200,626 B1 | 3/2001 | Grobe et al. |
| 6,213,604 B1 | 4/2001 | Valint et al. |
| 6,312,393 B1 | 11/2001 | Abreu |
| 6,348,507 B1 | 2/2002 | Heiler et al. |
| 6,366,794 B1 | 4/2002 | Moussy et al. |
| 6,423,001 B1 | 7/2002 | Abreu |
| 6,428,839 B1 | 8/2002 | Kunzler et al. |
| 6,431,705 B1 | 8/2002 | Linden |
| 6,440,571 B1 | 8/2002 | Valint et al. |
| 6,450,642 B1 | 9/2002 | Jethmalani et al. |
| 6,532,298 B1 | 3/2003 | Cambier et al. |
| 6,550,915 B1 | 4/2003 | Grobe, III |
| 6,570,386 B2 | 5/2003 | Goldstein |
| 6,579,235 B1 | 6/2003 | Abita et al. |
| 6,579,918 B1 | 6/2003 | Auten et al. |
| 6,599,559 B1 | 7/2003 | McGee et al. |
| 6,614,408 B1 | 9/2003 | Mann |
| 6,630,243 B2 | 10/2003 | Valint et al. |
| 6,638,563 B2 | 10/2003 | McGee et al. |
| 6,726,322 B2 | 4/2004 | Andino et al. |
| 6,735,328 B1 | 5/2004 | Helbing et al. |
| 6,779,888 B2 | 8/2004 | Marmo |
| 6,804,560 B2 | 10/2004 | Nisch et al. |
| 6,851,805 B2 | 2/2005 | Blum et al. |
| 6,885,818 B2 | 4/2005 | Goldstein |
| 6,939,299 B1 | 9/2005 | Petersen et al. |
| 6,980,842 B2 | 12/2005 | March et al. |
| 7,018,040 B2 | 3/2006 | Blum et al. |
| 7,131,945 B2 | 11/2006 | Fink et al. |
| 7,169,106 B2 | 1/2007 | Fleischman et al. |
| 7,398,119 B2 | 7/2008 | Lambert et al. |
| 7,423,801 B2 | 9/2008 | Kaufman et al. |
| 7,429,465 B2 | 9/2008 | Muller et al. |
| 7,441,892 B2 | 10/2008 | Hsu |
| 7,443,016 B2 | 10/2008 | Tsai et al. |
| 7,450,981 B2 | 11/2008 | Jeon |
| 7,639,845 B2 | 12/2009 | Utsunomiya |
| 7,654,671 B2 | 2/2010 | Glynn |
| 7,699,465 B2 | 4/2010 | Dootjes et al. |
| 7,728,949 B2 | 6/2010 | Clarke et al. |
| 7,751,896 B2 | 7/2010 | Graf et al. |
| 7,799,243 B2 | 9/2010 | Mather et al. |
| 7,809,417 B2 | 10/2010 | Abreu |
| 7,878,650 B2 | 2/2011 | Fritsch et al. |
| 7,885,698 B2 | 2/2011 | Feldman |
| 7,907,931 B2 | 3/2011 | Hartigan et al. |
| 7,926,940 B2 | 4/2011 | Blum et al. |
| 7,931,832 B2 | 4/2011 | Pugh et al. |
| 7,964,390 B2 | 6/2011 | Rozakis et al. |
| 8,080,187 B2 | 12/2011 | Tepedino, Jr. et al. |
| 8,096,654 B2 | 1/2012 | Amirparviz et al. |
| 8,118,752 B2 | 2/2012 | Hetling et al. |
| 8,142,016 B2 | 3/2012 | Legerton et al. |
| 8,224,415 B2 | 7/2012 | Budiman |
| 9,289,954 B2 * | 3/2016 | Linhardt ............... A61B 5/6821 |
| 2002/0193674 A1 | 12/2002 | Fleischman et al. |
| 2003/0179094 A1 | 9/2003 | Abreu |
| 2004/0027536 A1 | 2/2004 | Blum et al. |
| 2004/0116794 A1 | 6/2004 | Fink et al. |
| 2004/0207808 A1 * | 10/2004 | Fleischman ............... A61B 3/16 |
| | | 351/159.18 |
| 2005/0045589 A1 | 3/2005 | Rastogi et al. |
| 2005/0221276 A1 | 10/2005 | Rozakis et al. |
| 2006/0183986 A1 | 8/2006 | Rice et al. |
| 2007/0016074 A1 | 1/2007 | Abreu |
| 2007/0030443 A1 | 2/2007 | Chapoy et al. |
| 2007/0121065 A1 | 5/2007 | Cox et al. |
| 2007/0188710 A1 | 8/2007 | Hetling et al. |
| 2008/0208335 A1 | 8/2008 | Blum et al. |
| 2008/0218696 A1 | 9/2008 | Mir |
| 2009/0033863 A1 | 2/2009 | Blum et al. |
| 2009/0036761 A1 | 2/2009 | Abreu |
| 2009/0057164 A1 | 3/2009 | Minick et al. |
| 2009/0076367 A1 | 3/2009 | Sit et al. |
| 2009/0118604 A1 | 5/2009 | Phan et al. |
| 2009/0189830 A1 | 7/2009 | Deering et al. |
| 2009/0196460 A1 | 8/2009 | Jakobs et al. |
| 2009/0206498 A1 | 8/2009 | Tepedino, Jr. et al. |
| 2010/0001926 A1 | 1/2010 | Amirparviz et al. |
| 2010/0013114 A1 | 1/2010 | Bowers et al. |
| 2010/0016704 A1 | 1/2010 | Naber et al. |
| 2010/0028559 A1 | 2/2010 | Yan et al. |
| 2010/0072643 A1 | 3/2010 | Pugh et al. |
| 2010/0109175 A1 | 5/2010 | Pugh et al. |
| 2010/0110372 A1 | 5/2010 | Pugh et al. |
| 2010/0113901 A1 | 5/2010 | Zhang et al. |
| 2010/0133510 A1 | 6/2010 | Kim et al. |
| 2010/0249548 A1 | 9/2010 | Muller |
| 2011/0015512 A1 | 1/2011 | Pan et al. |
| 2011/0028807 A1 | 2/2011 | Abreu |
| 2011/0040161 A1 | 2/2011 | Abreu |
| 2011/0055317 A1 | 3/2011 | Vonog et al. |
| 2011/0063568 A1 | 3/2011 | Meng et al. |
| 2011/0084834 A1 | 4/2011 | Sabeta |
| 2011/0116035 A1 | 5/2011 | Fritsch et al. |
| 2011/0157541 A1 | 6/2011 | Peyman |
| 2011/0157544 A1 | 6/2011 | Pugh et al. |
| 2011/0184271 A1 | 7/2011 | Veciana et al. |
| 2011/0274680 A1 | 11/2011 | Mazed et al. |
| 2011/0286064 A1 | 11/2011 | Burles et al. |
| 2011/0298794 A1 | 12/2011 | Freedman |
| 2012/0026458 A1 | 2/2012 | Qiu et al. |

(56) References Cited

U.S. PATENT DOCUMENTS

| | | | |
|---|---|---|---|
| 2012/0038881 A1 | 2/2012 | Amirparviz et al. | |
| 2012/0041287 A1 | 2/2012 | Goodall et al. | |
| 2012/0041552 A1 | 2/2012 | Chuck et al. | |
| 2012/0069254 A1 | 3/2012 | Burton | |
| 2012/0075168 A1 | 3/2012 | Osterhout et al. | |
| 2012/0075574 A1 | 3/2012 | Pugh et al. | |
| 2012/0078071 A1 | 3/2012 | Bohm et al. | |
| 2012/0088258 A1 | 4/2012 | Bishop et al. | |
| 2012/0092612 A1 | 4/2012 | Binder | |
| 2012/0109296 A1* | 5/2012 | Fan | A61F 2/14 623/6.63 |
| 2012/0177576 A1 | 7/2012 | Hu | |
| 2012/0199995 A1* | 8/2012 | Pugh | A61N 5/0618 264/1.36 |
| 2012/0201755 A1 | 8/2012 | Rozakis et al. | |
| 2012/0245444 A1* | 9/2012 | Otis | A61B 5/1486 600/345 |
| 2012/0259188 A1* | 10/2012 | Besling | A61B 5/14507 600/319 |
| 2013/0135578 A1* | 5/2013 | Pugh | G02C 7/04 351/159.39 |
| 2014/0200424 A1* | 7/2014 | Etzkorn | A61B 5/14532 600/345 |

FOREIGN PATENT DOCUMENTS

| | | |
|---|---|---|
| EP | 1061874 | 12/2000 |
| EP | 1818008 | 8/2007 |
| EP | 1947501 | 7/2008 |
| EP | 1617757 | 8/2009 |
| EP | 2457122 | 5/2012 |
| WO | 95/04609 | 2/1995 |
| WO | 01/16641 | 3/2001 |
| WO | 01/34312 | 5/2001 |
| WO | 03/065876 | 8/2003 |
| WO | 2004/060431 | 7/2004 |
| WO | 2004064629 | 8/2004 |
| WO | 2006/015315 | 2/2006 |
| WO | 2009/094643 | 7/2009 |
| WO | 2010/105728 | 9/2010 |
| WO | 2010/133317 | 11/2010 |
| WO | 2011/011344 | 1/2011 |
| WO | 2011/034592 | 3/2011 |
| WO | 2011/035228 | 3/2011 |
| WO | 2011/035262 | 3/2011 |
| WO | 2011/083105 | 7/2011 |
| WO | 2011/163080 | 12/2011 |
| WO | 2012/035429 | 3/2012 |
| WO | 2012/037455 | 3/2012 |
| WO | 2012/051167 | 4/2012 |
| WO | 2012/051223 | 4/2012 |
| WO | 2012052765 | 4/2012 |

OTHER PUBLICATIONS

Carlson et al., "A 20 mV Input Boost Converter With Efficient Digital Control for Thermoelectric Energy Harvesting," IEEE Journal of Solid-State Circuits, Apr. 2010, pp. 741-750, vol. 45, No. 4.
Chu et al., "Biomedical soft contact-lens sensor for in situ ocular biomonitoring of tear contents," Biomed Microdevices, 2011, pp. 603-611, vol. 13.
Chu et al., "Soft contact lens biosensor for in situ monitoring of tear glucose as non-invasive blood sugar assessment," Talanta, 2011, pp. 960-965, vol. 83.
Ho et al., "Contact Lens With Integrated Inorganic Semiconductor Devices," MEMS 2008. IEEE 21st International Conference on. IEEE, 2008., pp. 403-406.
Lähdesmäki et al., "Possibilities for Continuous Glucose Monitoring by a Functional Contact Lens," IEEE Instrumentation & Measurement Magazine, Jun. 2010, pp. 14-17.
Lingley et al., "A contact lens with integrated micro solar cells," Microsyst Technol, 2012, pp. 453-458, vol. 18.
Parviz, Babak A., "For Your Eyes Only," IEEE Spectrum, Sep. 2009, pp. 36-41.
Saeedi, E. et al., "Self-assembled crystalline semiconductor optoelectronics on glass and plastic," J. Micromech. Microeng., 2008, pp. 1-7, vol. 18.
Saeedi et al., "Self-Assembled Inorganic Micro-Display on Plastic," Micro Electro Mechanical Systems, 2007. MEMS. IEEE 20th International Conference on. IEEE, 2007., pp. 755-758.
Sensimed Triggerfish, Sensimed Brochure, 2010, 10 pages.
Shih, Yi-Chun et al., "An Inductorless DC-DC Converter for Energy Harvesting With a 1.2µW Bandgap-Referenced Output Controller," IEEE Transactions on Circuits and Systems-II: Express Briefs, Dec. 2011, pp. 832-836, vol. 58, No. 12.
Shum et al., "Functional modular contact lens," Proc. of SPIE, 2009, pp. 73970K-1 to 73970K-8, vol. 7397.
Stauth et al., "Self-assembled single-crystal silicon circuits on plastic," PNAS, Sep. 19, 2006, pp. 13922-13927, vol. 103, No. 38.
Yao, H. et al., "A contact lens with integrated telecommunication circuit and sensors for wireless and continuous tear glucose monitoring," J. Micromech. Microeng., 2012, pp. 1-10, vol. 22.
Yao, H. et al., "A Dual Microscal Glucose Sensor on a Contact Lens, Tested in Conditions Mimicking the Eye," Micro Electro Mechanical Systems (MEMS), 2011 IEEE 24th International Conference on. IEEE, 2011, pp. 25-28.
Yao et al., "A contact lens with embedded sensor for monitoring tear glucose level," Biosensors and Bioelectronics, 2011, pp. 3290-3296, vol. 26.
Yao, H. et al., "A Soft Hydrogel Contact Lens with an Encapsulated Sensor for Tear Glucose Monitoring," Micro Electro Mechanical Systems (MEMS), 2012 IEEE 25th International Conference on. IEEE, 2012, pp. 769-772.
Yeager et al., "A 9 µA, Addressable Gen2 Sensor Tag for Biosignal Acquistion," IEEE Journal of Solid-State Circuits, Oct. 2010, pp. 2198-2209, vol. 45, No. 10.
Zhang et al., "Design for Ultra-Low Power Biopotential Amplifiers for Biosignal Acquistion Applications," IEEE Transactions on Biomedical Circuits and Systems, 2012, pp. 344-355, vol. 6, No. 4.
Bionic contact lens 'to project emails before eyes,' http://www.kurzweilai.net forums/topic/bionic-contact-lens-to-project-emails-before-eyes, Last accessed Mar. 14, 2012, 2 pages.
Brahim, et al., "Polypyrrole-hydrogel composites for the construction of clinically important biosensors," 2002, Biosensors & Bioelectronics, pp. 53-59, vol. 17.
Chen, et al., "Microfabricated Implantable Parylene-Based Wireless Passive Intraocular Pressure Sensors," Journal of Microelectromechanical Systems, Dec. 2008, pp. 1342-1351, vol. 17, No. 6.
Chu, et al., "Soft Contact-lens Sensor for Monitoring Tear Sugar as Novel Wearable Device of Body Sensor Network," http://www.ksi edu/seke/dms11/DMS/2_Kohji_Mitsubayashi.pdf, Last accessed Jul. 27, 2012, 4 pages.
"Contact Lenses: Look Into My Eyes," The Economist, Jun. 2, 2011, http://www.economist.com/node/18750624/print, Last accessed Mar. 13, 2012, 8 pages.
Haders, "New Controlled Release Technologies Broaden Opportunities for Ophthalmic Therapies," Drug Delivery Technology, Jul./Aug. 2009, pp. 48-53, vol. 8, No. 7.
Holloway, "Microsoft developing electronic contact lens to monitor blood sugar," Gizmag, Jan. 5, 2012, http://www.gizmag.com/microsoft-electronic-diabetic-contact-lens/20987/, Last accessed Mar. 13, 2012. 5 pages.
Huang, et al., "Wrinkling of Ultrathin Polymer Films," Mater. Res. Soc. Symp. Proc., 2006, 6 pages, vol. 924, Materials Research Society.
Hurst, "How contact lenses could help save your life," Mail Online, Apr. 19, 2010, http://www.dailymail.co.uk/health/article-1267345/How-contact-lenses-help-save-life.html, Last accessed Jul. 27, 2012.
Liao, et al., "A 3-µW CMOS Glucose Sensor for Wireless Contact-Lens Tear Glucose Monitoring ," IEEE Journal of Solid-State Circuits, Jan. 2012, pp. 335-344, vol. 47, No. 1.
Liao, et al., "A 3-µW Wirelessly Powered CMOS Glucose Sensor for an Active Contact Lens," 2011 IEEE International Solid-State Circuits Conference, Session 2, Feb. 21, 2011, 3 pages.
Lingley, et al., "A Single-Pixel Wireless Contact Lens Display," Journal of Micromechanics and Microengineering, 2011, pp. 1-8.

(56) References Cited

OTHER PUBLICATIONS

Lingley, et al., "Multipurpose integrated active contact lenses," SPIE, 2009, 2 pages.
Liu, et al., "Miniature Amperometric Self-Powered Continuous Glucose Sensor with Linear Response," Analytical Chemistry, 2012, 7 pages.
Loncar, et al., "Design and Fabrication of Silicon Photonic Crystal Optical Waveguides," Journal of Lightwave Technology, Oct. 2000, pp. 1402-1411, vol. 18, No. 10.
Murdan, "Electro-responsive drug delivery from hydrogels," Journal of Controlled Release, 2003, pp. 1-17, vol. 92.
Pandey, et al., "A Fully Integrated RF-Powered Contact Lens With a Single Element Display," IEEE Transactions on Biomedical Circuits and Systems, Dec. 2010, pp. 454-461, vol. 4, No. 6.
Parviz, Babak A., "Augmented Reality in a Contact Lens," IEEE Spectrum, Sep. 2009, http://spectrum.ieee.org/biomedical/bionics/augmented-reality-in-a-contact-lens/0, Last accessed Mar. 14, 2012, 6 pages.
Selner, et al., "Novel Contact Lens Electrode Array for Multi-electrode Electroretinography (meERG)," IEEE, 2011, 2 pages.
Singh, et al., "Novel Approaches in Formulation and Drug Delivery using Contact Lenses," Journal of Basic and Clinical Pharmacy, May 2011, pp. 87-101, vol. 2, Issue 2.
Thomas, et al., "Functional Contact Lenses for Remote Health Monitoring in Developing Countries," IEEE Global Humanitarian Technology Conference, 2011, pp. 212-217, IEEE Computer Society.
Tweedie, et al., "Contact creep compliance of viscoelastic materials via nanoindentation," J. Mater. Res., Jun. 2006, pp. 1576-1589, vol. 21, No. 2, Materials Research Society.
Wall, K., "Active contact lens that lets you see like the Terminator patented," Feb. 10, 2012, http://vvww.patexia.com/feed/active-contact-lens-that-lets-you-see-like-the-terminator-patented-2407, Last accessed Mar. 28, 2012, 5 pages.
Zarbin, et al., "Nanotechnology in ophthalmology," Can J Ophthalmol, 2010, pp. 457-476, vol. 45, No. 5.

* cited by examiner

US 9,636,016 B1

EYE-MOUNTABLE DEVICES AND METHODS FOR ACCURATELY PLACING A FLEXIBLE RING CONTAINING ELECTRONICS IN EYE-MOUNTABLE DEVICES

BACKGROUND

Unless otherwise indicated herein, the materials described in this section are not prior art to the claims in this application and are not admitted to be prior art by inclusion in this section.

An eye-mountable device may be configured to monitor health-related information based on at least one analyte detected in a tear film of a user wearing the eye-mountable device. For example, the eye-mountable device may be in the form of a contact lens that includes a sensor configured to detect the at least one analyte (e.g., glucose). The eye-mountable device may also be configured to monitor various other types of health-related information.

SUMMARY

In one aspect, an example method involves: forming a first polymer layer, wherein the first polymer layer defines a posterior side of an eye-mountable device; positioning a ring-shaped structure on the first polymer layer in a predetermined rotational orientation, wherein the ring-shaped structure comprises a sensor configured to detect an analyte; forming a second polymer layer over the first polymer layer and the ring-shaped structure, such that the ring-shaped structure is fully enclosed by the first polymer layer and the second polymer layer, wherein the second polymer layer defines an anterior side of the eye-mountable device; and forming a channel through the second polymer layer based on the predetermined rotational orientation, such that the sensor is configured to receive the analyte via the channel.

In another aspect, an example method involves: forming a first polymer layer, wherein the first polymer layer defines a posterior side of an eye-mountable device; positioning a ring-shaped structure on the first polymer layer in a predetermined rotational orientation, wherein the ring-shaped structure comprises a sensor configured to detect an analyte; forming a mask layer over the sensor, such that the sensor is enclosed by the mask layer; forming a second polymer layer over the first polymer layer and the ring-shaped structure, such that the ring-shaped structure is fully enclosed by the first polymer layer and the second polymer layer except for the sensor being enclosed by the mask layer, wherein the second polymer layer defines an anterior side of the eye-mountable device; and removing the mask layer to form a channel through the second polymer layer based on the predetermined rotational orientation, such that the sensor is configured to receive the analyte via the channel.

In yet another aspect, an eye-mountable device is disclosed. An example eye-mountable device includes: a transparent polymer, wherein the transparent polymer defines a posterior side and an anterior side of the eye-mountable device, and wherein the anterior side includes a channel; and a ring-shaped structure embedded in the transparent polymer, the ring-shaped structure having an outer diameter and an asymmetric inner diameter and including a sensor configured to detect an analyte, wherein the asymmetric inner diameter defines a rotational orientation of the ring-shaped structure relative to the channel, such that the sensor is configured to receive the analyte through the channel.

These as well as other aspects, advantages, and alternatives, will become apparent to those of ordinary skill in the art by reading the following detailed description, with reference where appropriate to the accompanying drawings.

DETAILED DESCRIPTION

The following detailed description describes various features and functions of the disclosed systems and methods with reference to the accompanying figures. In the figures, similar symbols typically identify similar components, unless context dictates otherwise. The illustrative method and system embodiments described herein are not meant to be limiting. It will be readily understood that certain aspects of the disclosed methods and systems can be arranged and combined in a wide variety of different configurations, all of which are contemplated herein.

I. Introduction

An eye-mountable device may be configured to monitor health-related information based on at least one analyte detected in a tear film of a user wearing the eye-mountable device. Such an eye-mountable device may include a sensor configured to detect the at least one analyte. The sensor can receive the at least one analyte through a channel in a polymer layer of the eye-mountable device.

When fabricating such an eye-mountable device, precise placement of a sensor relative to a channel in a polymer layer may be desired. For instance, it may be desirable for the sensor to be placed at an end of the channel, such that the sensor can receive at least one analyte through the channel. Beneficially, the disclosed methods and systems allow for placement of the sensor in a desired position relative to the channel, such as a predetermined rotational orientation.

As used throughout this disclosure, the anterior side of the eye-mountable device refers to an outward-facing side of the eye-mountable device, whereas the posterior side of the eye-mountable device refers to an inward-facing side of the eye-mountable device. In particular, when the eye-mountable device is mounted on an eye of the user, the anterior side corresponds to a side of the eye-mountable device that is facing outward and thus not touching the eye of the user. Further, when the eye-mountable device is mounted on an eye of the user, the posterior side corresponds to a side of the eye-mountable device that is facing inward and thus touching the eye of the user.

II. Example Methods

Figure 1:
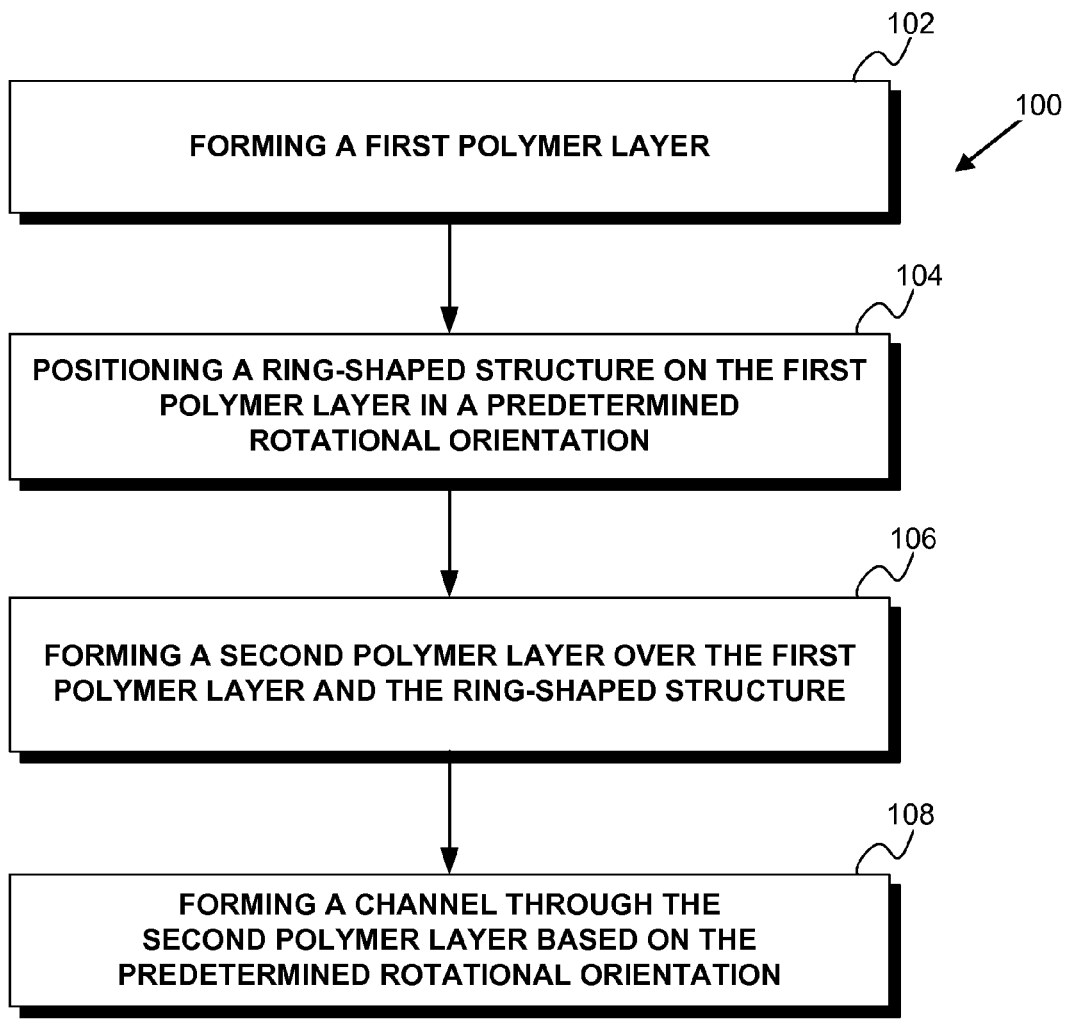
FIG. 1 is a flow chart illustrating an example method according to an example embodiment.

Example methods for fabricating an eye-mountable device are disclosed. FIG. 1 is a flow chart illustrating a method according to an example embodiment. More specifically, example method 100 involves forming a first polymer layer, as shown by block 102. Example method 100 may then involve positioning a ring-shaped structure on the first polymer layer in a predetermined rotational orientation, as shown by block 104. Further, example method 100 may then involve forming a second polymer layer over the first polymer layer and the ring-shaped structure, as shown by block 106. Example method 100 may then involve forming a channel through the second polymer layer based on the predetermined rotational orientation, as shown by block 108.

For purposes of illustration, example method 100 is described below as being carried out by a fabrication device that utilizes cast or compression molding. It should be understood, however, that example method 100 may be carried out by a fabrication device that utilizes other methods for forming the polymer layers.

A. Forming a First Polymer Layer

Figure 2A:
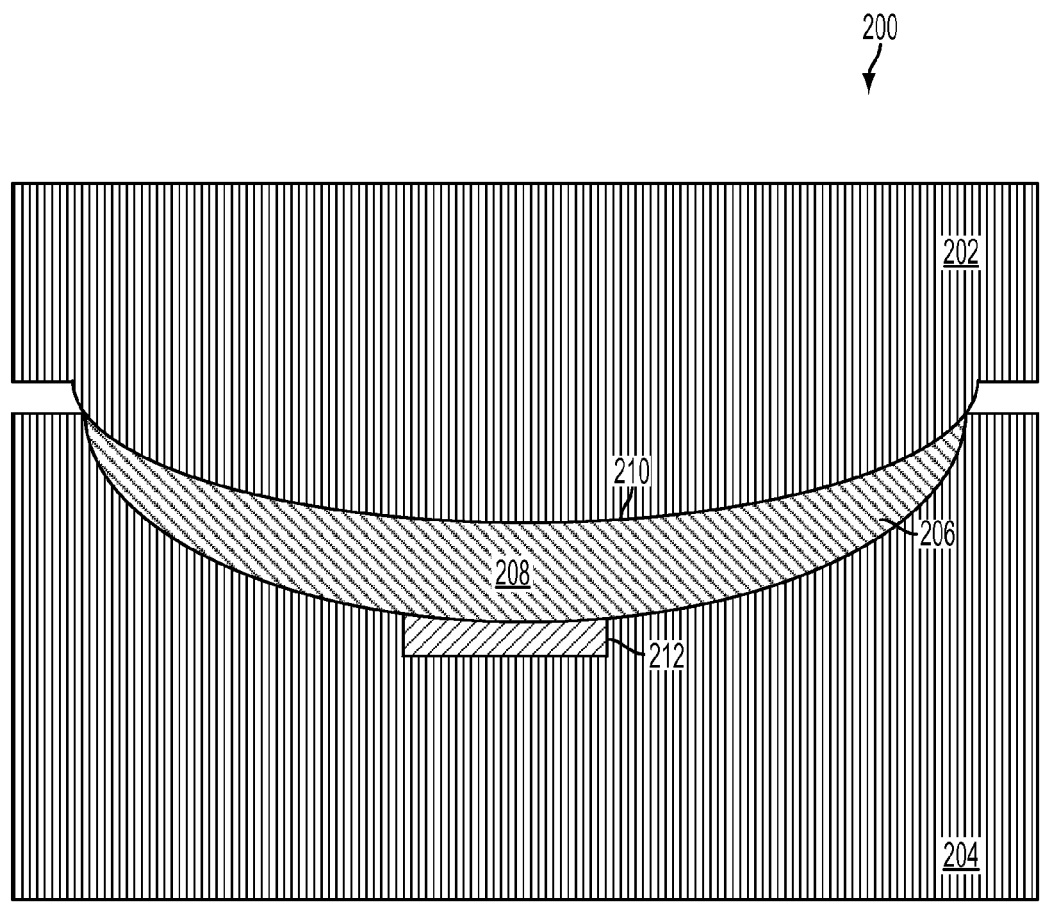
FIG. 2a is an illustration of formation of a first polymer layer, according to an example embodiment.

As mentioned above, at block 102, the fabrication device may be used to form a first polymer layer. The fabrication device may include molding pieces, such as molding pieces that are suitable for cast molding. FIG. 2a illustrates an example fabrication device 200 that includes example molding pieces that may be used to form the first polymer layer. In particular, FIG. 2a illustrates example fabrication device 200 including a first molding piece 202 and a second molding piece 204. The first molding piece 202 and the second molding piece 204 may define a first cavity. The second molding piece 204 may be filled with a polymer material 206, and the polymer material 206 may be compressed into a first polymer layer 208 by the first molding piece 202.

After the polymer material 206 is compressed into the first polymer layer 208, example fabrication device 200 may cure the first polymer layer 208. Curing involves the hardening of a polymer material by cross-linking of polymer chains, and curing may be, for example, brought about by chemical additives, ultraviolet radiation, electron beam, and/or heat. In an example, the polymer material 206 can be a light-curable polymer material, and example fabrication device 200 may be configured to cure the light-curable polymer material using light, such as ultraviolet light or visible light.

In an example, the first polymer layer 208 may be cured to a partially-cured state. In an example, this may involve curing the material to a partially-cured state that is approximately 50-75% of a fully cured state. Other partially-cured states are possible as well. Beneficially, by partially curing the first polymer layer to a partially-cured state, the first polymer layer 208 may have a tackiness that facilitates adhesion thereto. With this arrangement, the tackiness may ensure that a ring-shaped structure placed on the first polymer layer 208 remains securely fixed in a given location during subsequent formation steps.

The tackiness exhibited by the partially-cured first polymer layer 208 may be different for different polymers. Accordingly, example fabrication device 200 may be configured to cure different polymer materials differently than other polymer materials (e.g., a first polymer material may be cured more than a second polymer material). Further, in addition to light curing, other methods of curing are possible as well, such as chemical additives and/or heat. Yet still further, in other example embodiments, the first polymer layer may be completely cured. Alternatively, example fabrication device 200 may bypass the curing process at this stage.

The first molding piece 202 and the second molding piece 204 may be configured to achieve a given desired thickness of the first polymer layer 208. For instance, in an example, the first polymer layer 208 can have a thickness of less than 150 micrometers. In an example embodiment, the first molding piece 202 and the second molding piece 204 can be designed so as to allow for a layer having less than a 150 micrometer thickness between the two cavities. As such, when the first molding piece 202 and the second molding piece 204 are pressed together during the formation of the first polymer layer 208, the resulting polymer layer 208 will have a thickness of less than 150 micrometers.

In an example, the thickness of the first polymer layer 208 can be selected based on a particular analyte or analytes an eye-mountable device is configured to detect. For example, an optimal thickness for a first analyte may be 10 micrometers, while an optimal thickness for a second analyte may be 25 micrometers. Other examples are possible as well.

In an example, the polymer material 206 can be any material that can form an eye-compatible polymer layer. For example, the polymer material 206 may be a formulation containing polymerizable monomers, such as hydrogels, silicone hydrogels, silicone elastomers, and rigid gas permeable materials. Further, the polymer material 206 may form a transparent or substantially transparent polymer layer. As such, the use of the polymer material 206 may result in an eye-mountable device through which the wearer can see when mounted on the wearer's eye. In an example, the polymer material 206 can be a hydrogel material, such as silicone hydrogel. As known in the art, hydrogel materials are commonly used in contact-lens technology and are well-suited for eye-mountable devices. Other materials are possible as well.

In an example, the first molding piece 202 and/or the second molding piece 204 can be configured so as to allow sufficient pinch off to provide for suitable edges for an eye-mountable device.

The first polymer layer 208 defines a posterior side 210 of an eye-mountable device. That is, the first polymer layer 208 defines an outer edge of the eye-mountable device. When mounted on an eye of a user, the posterior side 210 of the eye-mountable device defined by the first polymer layer 208 corresponds to a side of the device touching the eye of the user. The first molding piece 202 may be shaped so as to define a shape of the posterior side 210. For example, a curvature of the posterior side 210 may be defined by the first molding piece 202.

The first polymer layer 208 can further comprise an alignment feature 212. In an example, the alignment feature 212 can comprise an asymmetric peg. The asymmetric peg can be a variety of shapes. For instance, the asymmetric peg can have a star-shaped or cross-shaped cross section. Other shapes of the asymmetric peg are possible as well.

As mentioned above, although FIG. 2a illustrates forming the first polymer layer 208 through cast molding, other methods for forming first polymer layer 208 are possible as well. For example, the first polymer layer 208 may be formed via injection molding. In injection molding, rather than polymer material being compressed between molding pieces, molding material may be heated and injected or otherwise forced into a molding piece or pieces. The injected molding material may then cool and harden to the configuration of the molding piece or pieces.

As another example, the first polymer layer 208 may be formed via spin casting. Through spin-casting techniques, the fabrication device may form a first polymer layer of a precise thickness. In an example, a spin-casting mold may be spun along its central access at a set speed, and the polymer may be introduced to the mold as the mold is spinning in order to form a first polymer layer. The final thickness of the first polymer layer may be influenced by various factors, including but not limited to the spin-casting mold, the amount of polymer introduced to the spin-casting mold, properties of the polymer such as viscosity, and/or the speed at which the spin-casting mold is rotated. These factors may be varied in order to result in a first polymer layer of a well-defined thickness.

Figure 2B:
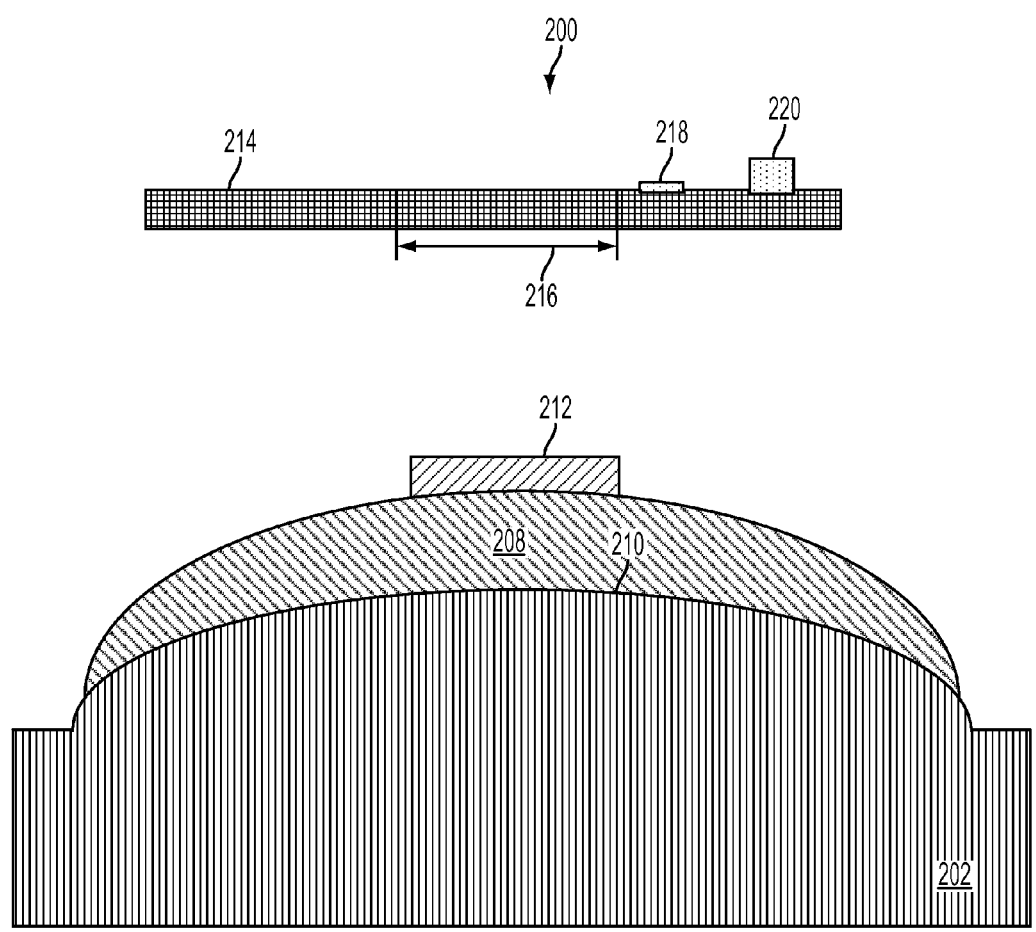
FIG. 2b is an illustration of positioning a ring-shaped structure on a first polymer layer in a predetermined rotational orientation, according to an example embodiment.
Figure 2C:
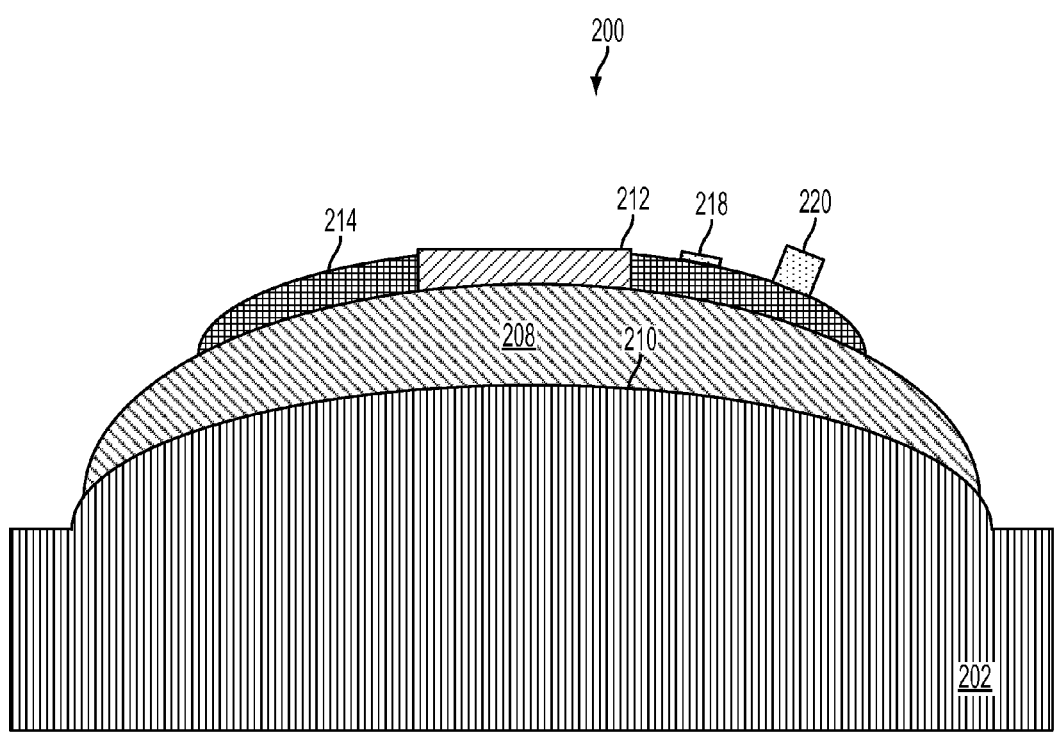
FIG. 2c is an illustration of a ring-shaped structure positioned on a first polymer layer in a predetermined rotational orientation, according to an example embodiment.

B. Positioning a Ring-Shaped Structure on the First Polymer Layer in a Predetermined Rotational Orientation As mentioned above, at block 104, a ring-shaped structure may be positioned on the first polymer layer in a predetermined rotational orientation. FIGS. 2b and 2c illustrate an example in which a ring-shaped structure 214 is positioned on the first polymer layer 208 in a predetermined rotational orientation.

In an example, the ring-shaped structure 214 can have an outer diameter and a hole 216 that defines an inner diameter. The ring-shaped structure 214 can further include a sensor 218 and electronics 220 that are each mounted thereon. The ring-shaped structure 214 may occupy a peripheral portion of an eye-mountable device, such as an example eye-mountable device 300 illustrated in FIG. 3, so as to limit interference with a user's field of view when the eye-mountable device is mounted on an eye of the user. The ring-shaped structure 214 may comprise a polymeric material, such as paralyene. In some examples, the ring-shaped structure 214 may be more rigid than the first polymer layer 208.

The sensor 218 can be configured in a variety of ways. As one example, the sensor 218 may comprise a pair of electrodes, such as a working electrode and a reference electrode. Other configurations of the sensor 218 are possible as well. The sensor 218 can have a variety of thicknesses. As one example, the sensor 218 can have a thickness of 200 nanometers. Other thicknesses of the sensor 218 are possible as well.

The electronics 220 can be configured in a variety of ways. As one example, the electronics 220 can comprise a chip including one or more logic elements configured to operate the sensor 218. Other configurations of the electronics 220 are possible as well.

In order to position the ring-shaped structure 214, example fabrication device 200 may separate the first molding piece 202 from the second molding piece 204. When example fabrication device 200 separates the first molding piece 202 from the second molding piece 204, the first polymer layer 208 may stick to a side of the first molding piece 202. In an example, the first polymer layer 208 and/or the first molding piece 202 can be surface treated, such that the first polymer layer 208 sticks to the side of the first molding piece 202. Additionally or alternatively, the second molding piece 204 can be surface treated, such that the first polymer layer 208 sticks to the side of the first molding piece 202.

In an example, positioning the ring-shaped structure 214 on the first polymer layer 208 in a predetermined rotational orientation can include aligning the ring-shaped structure 214 with the alignment feature 212. In one example, the hole 216 in the ring-shaped structure 214 has an asymmetric inner diameter and alignment feature 212 includes an asymmetric peg such that the hole 216 receives the alignment feature 212 in only the predetermined rotational orientation. However, other ways of providing the predetermined rotational orientation of the ring-shaped structure 214 by alignment with the alignment feature 212 are also possible.

Alternatively, example fabrication device 200 can include a positioning apparatus (not shown), such as a robotic system, configured to position the ring-shaped structure 214 on the first polymer layer 208 in a predetermined rotational orientation. For instance, the positioning apparatus may (i) pick up the ring-shaped structure 214 (e.g., via suction), (ii) position the ring-shaped structure 214 above the first polymer layer 208, and then (iii) lower the ring-shaped structure 214 toward the first polymer layer 208. When the ring-shaped structure 214 is positioned in the predetermined rotational orientation, the positioning apparatus may then release the ring-shaped structure 214 (e.g., by releasing the suction). With this approach, the first polymer layer 208 might not include the alignment feature 212.

The positioning apparatus may further include a vision system configured to assist with positioning the ring-shaped structure 214 on the first polymer layer 208 in a predetermined rotational orientation. Such a vision system may facilitate guiding the ring-shaped structure 214 to a precise location on the first polymer layer 208. In an example, the vision system can be appropriate for situations in which one or more production specifications for an eye-mountable device, such as example eye-mountable device 300, have requirements with very low tolerances related to the positioning of a sensor, such as the sensor 218, within the eye-mountable device 300.

During fabrication of an eye-mountable device, such as example eye-mountable device 300, it may be desirable for the ring-shaped structure 214 to remain in a fixed position during fabrication of the eye-mountable device. For instance, movement of the ring-shaped structure 214 during subsequent formation steps, such as formation of a second polymer layer, may result in improper placement of the ring-shaped structure 214 relative to the surrounding polymer layers. As one example, movement of the ring-shaped structure 214 during filling a mold piece with a polymeric material to form the second polymer layer and/or curing the second polymer layer can result in improper placement of the ring-shaped structure 214 relative to the surrounding polymer layers.

Therefore, in an example, an adhesive is applied to the ring-shaped structure 214 and/or the first polymer layer 208 before the ring-shaped structure 214 is placed on the first polymer layer 208. The applied adhesive may facilitate adhesion of the ring-shaped structure 214 to the first polymer layer 208. For instance, a small amount of adhesive may be applied to a cured first polymer layer 208, and the ring-shaped structure 214 may be positioned on the small amount of adhesive such that the ring-shaped structure 214 adheres to the first polymer layer 208. Additionally or alternatively, a small amount of adhesive may be applied to the ring-shaped structure 214, and the ring-shaped structure 214 may then be placed on the first polymer layer 208 (e.g., a cured first polymer layer) such that the ring-shaped structure 214 adheres to the first polymer layer 208. With this arrangement, the ring-shaped structure 214 may remain adhered to the first polymer layer 208 in a secure location during subsequent formation steps.

As noted above, in an example, the first polymer layer 208 in a partially-cured state may have a tackiness that facilitates adhesion thereto. With this arrangement, the ring-shaped structure 214 may remain adhered to the first polymer layer 208 in a secure location during subsequent formation steps.

In some situations, such as for large-scale production purposes, it may be desirable to not only place the ring-shaped 214 in a predetermined rotational orientation, but it may also be desirable to repeatedly place and maintain the ring-shaped structure 214 at this precise location for a plurality of eye-mountable devices. Beneficially, fabrication of an eye-mountable device in accordance with an example embodiment allows for such repeatable and precise positioning.

The ring-shaped structure 214 can have various sizes. For instance, the size of the ring-shaped structure 214 may depend on which analyte an eye-mountable device is configured to detect. In an example, the ring-shaped structure 214 is a substrate shaped as a ring with approximately a 1 centimeter diameter, a radial thickness of approximately 1 millimeter, and a maximum height of approximately 50 between 150 micrometers. Of course, other sizes of the ring-shaped structure 214 are possible as well.

In an example, the ring-shaped structure 214 has a height dimension of at least 50 micrometers. In other words, at some point of the ring-shaped structure 214, the height of the ring-shaped structure 214 may be at least 50 micrometers. In an example, this height dimension may correspond to a maximum height of the ring-shaped structure 214. In accordance with the present disclosure, the maximum height of the ring-shaped structure 214 corresponds to the height of the ring-shaped structure 214 at its highest point. For instance, in the example where the ring-shaped structure 214 comprises the sensor 218 and the electronics 220, the height of the ring-shaped structure 214 may vary (and thus the ring-shaped structure 214 may have various height dimensions). For example, the height of the ring-shaped structure 214 may be higher at a point where the electronics 220 is mounted on the ring-shaped structure 214, whereas the height may be lower at a point where there is no chip on the ring-shaped structure 214. In such an example, the maximum height may correspond to the point where the electronics 220 is mounted on the ring-shaped structure 214.

FIG. 2c illustrates the ring-shaped structure 214 positioned on the first polymer layer 208 in a predetermined rotational orientation. With this arrangement, the sensor 218 is mounted at a particular angle along a circumference of the first polymer layer 208. As a result, the sensor 218 may be placed at a precise location in an XYZ plane on the first polymer layer 208. As one example, the sensor 218 may rest at a 6 o'clock position of the first polymer layer 208. As another example, the at least one sensor 218 may rest at a 12 o'clock position of the first polymer layer 208.

Figure 2D:
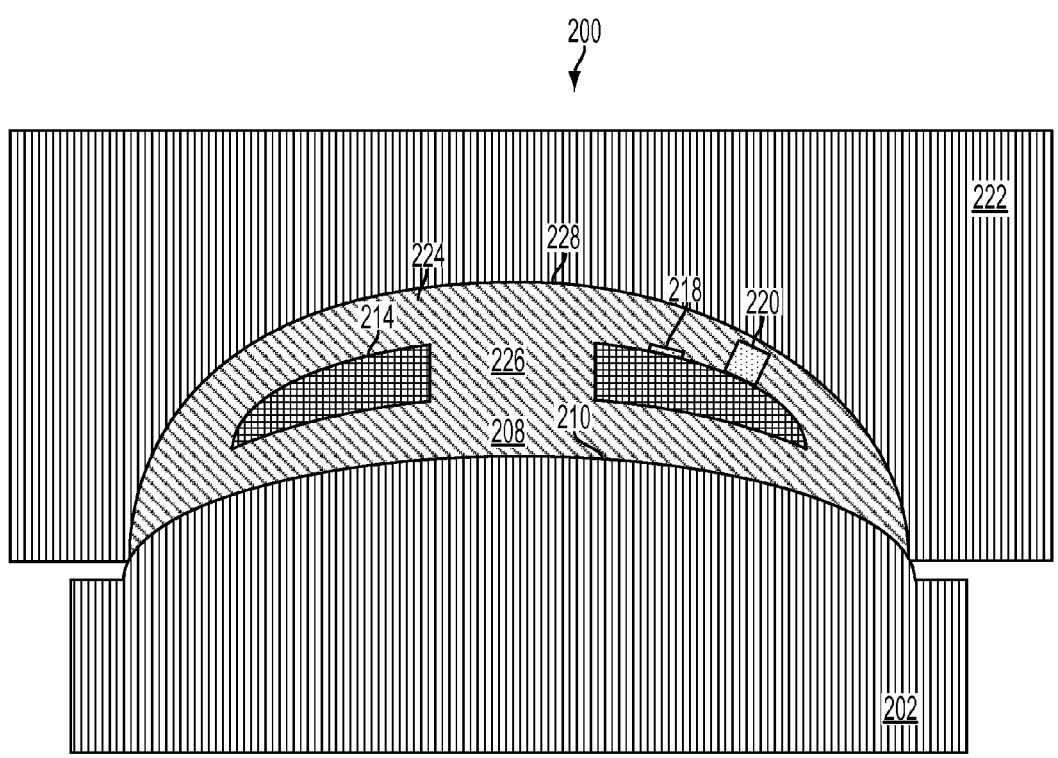
FIG. 2d is an illustration of formation of a second polymer layer, according to an example embodiment.

C. Forming a Second Polymer Layer Over the First Polymer Layer and the Ring-Shaped Structure As mentioned above, at block 106, the fabrication device may form a second polymer layer over the first polymer layer and the ring-shaped structure, such that the ring-shaped structure is fully enclosed by the first polymer layer and the second polymer layer. FIG. 2d illustrates example fabrication device 200 including example molding pieces that may be used to form the second polymer layer. In particular, FIG. 2d illustrates a third molding piece 222. The first molding piece 202 and the third molding piece 222 may define a second cavity.

The first molding piece 202, which already holds the first polymer layer 208 to which the ring-shaped structure 214 is mounted (as illustrated in FIG. 2c), may be filled with a polymer material 224. The polymer material 224 may be formed into a second polymer layer 226 by compression between the first molding piece 202 and the third molding piece 222. As a result, the second polymer layer 226 may mold over the ring-shaped structure 214, such that the ring-shaped structure 214 is fully enclosed by the first polymer layer 208 and the second polymer layer 226.

After the second polymer layer 226 is formed, example fabrication device 200 may cure the second polymer layer 226. In an example, the second polymer layer 226 can be cured like the first polymer layer 208. However, in other examples, the second polymer layer 226 may be cured by different techniques than the first polymer layer 208. The second polymer layer 226 can be cured by any of the techniques mentioned herein. In an example, example fabrication device 200 may cure the first polymer layer 208 at this stage.

Figure 3:
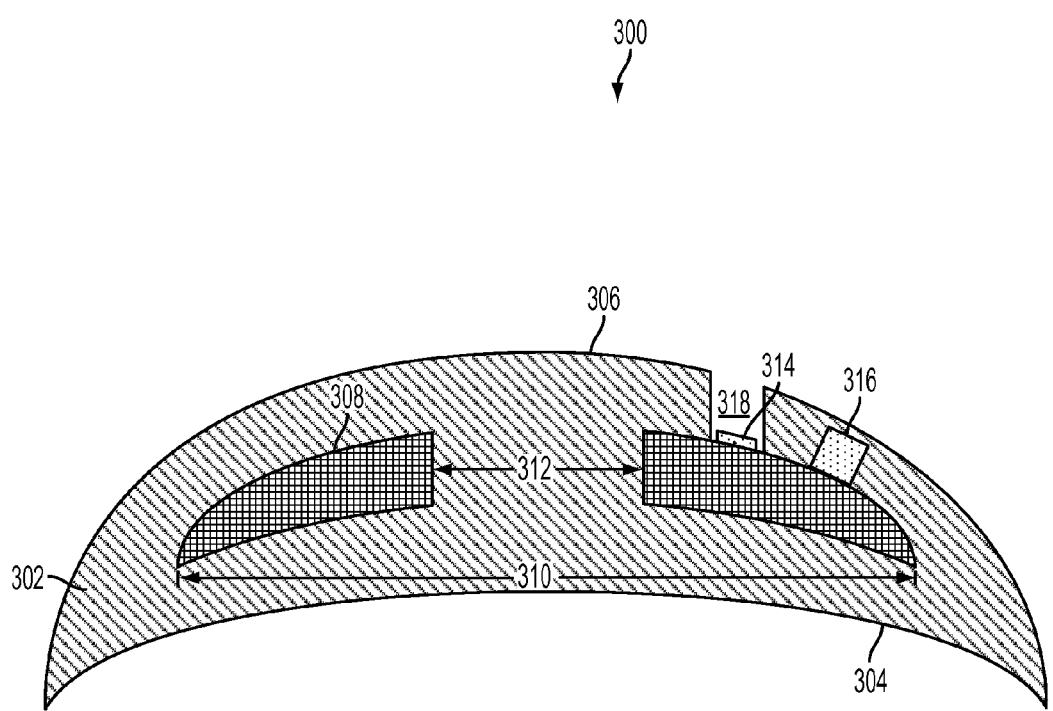
FIG. 3 is an illustration of an example eye-mountable device fabricated according to an example embodiment.

After the second polymer layer 226 is cured, there may not be a visible boundary line separating the first polymer layer 208 from the second polymer layer 226. As mentioned above, FIG. 3 illustrates example eye-mountable device 300. In particular, FIG. 3 illustrates example eye-mountable device 300 includes a transparent polymer 302. The transparent polymer 302 can be arranged like the first polymer layer 208 and the second polymer layer 226.

Returning to FIG. 2d, example fabrication device 200 may further comprise one or more alignment pins (not shown), such as a plurality of dowel pins, for aligning the third molding piece 222 and the first molding piece 202. The one or more alignment pins can assist in forming the second polymer layer 226 by aligning the third molding piece 222 with the first molding piece 202.

The first molding piece 202 and the third molding piece 222 may be configured to achieve a given desired thickness of a layer formed between the two pieces. As one example, the first molding piece 202 and the third molding piece 222 may be designed so as to define a thickness of the second polymer layer 226. As another example, the first molding piece 202 and the third molding piece 222 may be designed so as to define a final thickness of an eye-mountable device, such as example eye-mountable device 300. In an example, the first molding piece 202 and the third molding piece 222 can be designed so as to allow for a layer having a given desired thickness between the two pieces (in addition to a thickness of the first polymer 208). As such, when the first molding piece 202 and the third molding piece 222 are pressed together during formation of a layer, the resulting layer will have the given desired thickness.

In an example, the second polymer layer 226 has a thickness of greater than 50 micrometers. However, in other examples, the second polymer layer 226 can have a thickness between 50 and 300 micrometers, such as 130 micrometers. It should be understood that since the second polymer layer 226 molds over the ring-shaped structure 214, the second polymer layer 226 may not have a uniform thickness. For instance, the thickness of the second polymer layer 226 above the sensor 218 may be less than the thickness of the second polymer layer 226 that is not touching the sensor 218.

In an example, the thickness of the second polymer layer 226 can be selected based on a particular analyte or analytes that the eye-mountable device, such as example eye-mountable device 300, is configured to detect. For example, an optimal thickness for a first analyte may be 10 micrometers, while an optimal thickness for a second analyte may be 25 micrometers. Other examples are possible as well.

In an example, the second polymer layer 226 can be composed of the same polymer material as the first polymer layer 208. However, in other examples, the second polymer layer 226 can be composed of a different polymer material than the first polymer layer 208. The second polymer layer 226 can be any one of the polymer materials mentioned herein. In an example, the ring-shaped structure 214 can be more rigid than the second polymer layer 226.

The second polymer layer 226 defines an anterior side 228 of an eye-mountable device. That is, the second polymer layer 226 defines an outer edge of the eye-mountable device. When mounted on an eye of a user, the anterior side 228 of the eye-mountable device defined by the second polymer layer 226 corresponds to the side of the device that is not touching the eye of the user. The third molding piece 222 may be shaped so as to define a shape of the anterior side 228. For example, a curvature of the anterior side 228 may be defined by the third molding piece 222.

Figure 2E:
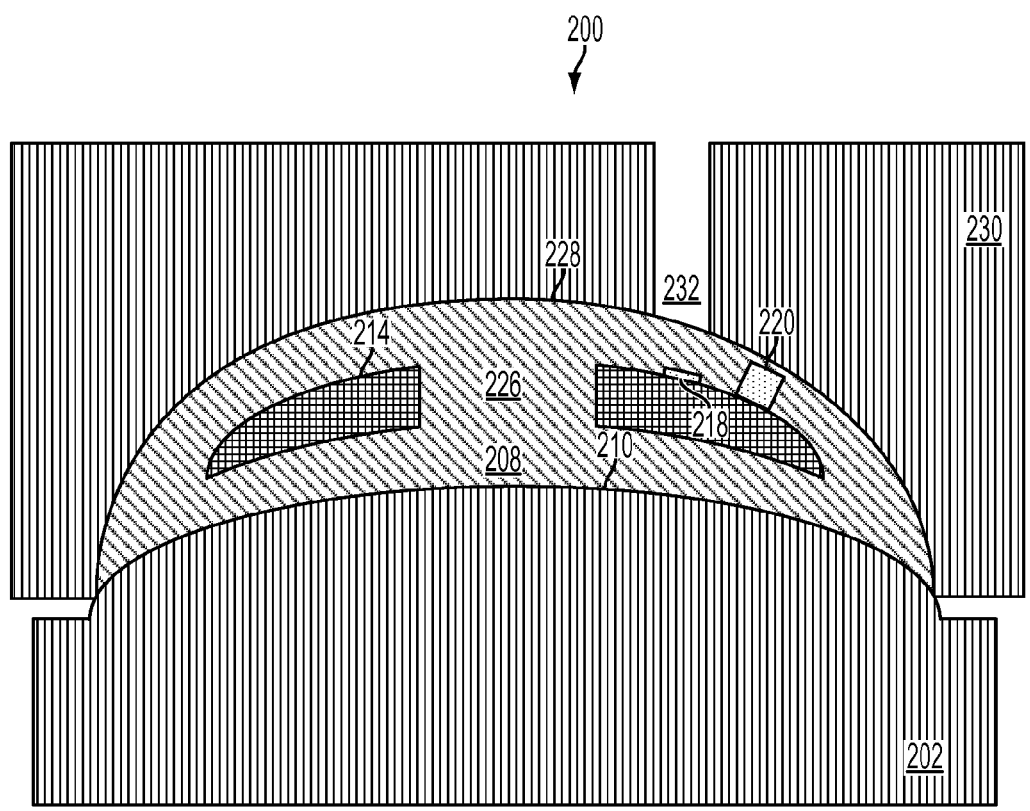
FIG. 2e is an illustration of a molding piece including a molding channel, according to an example embodiment.
Figure 2F:
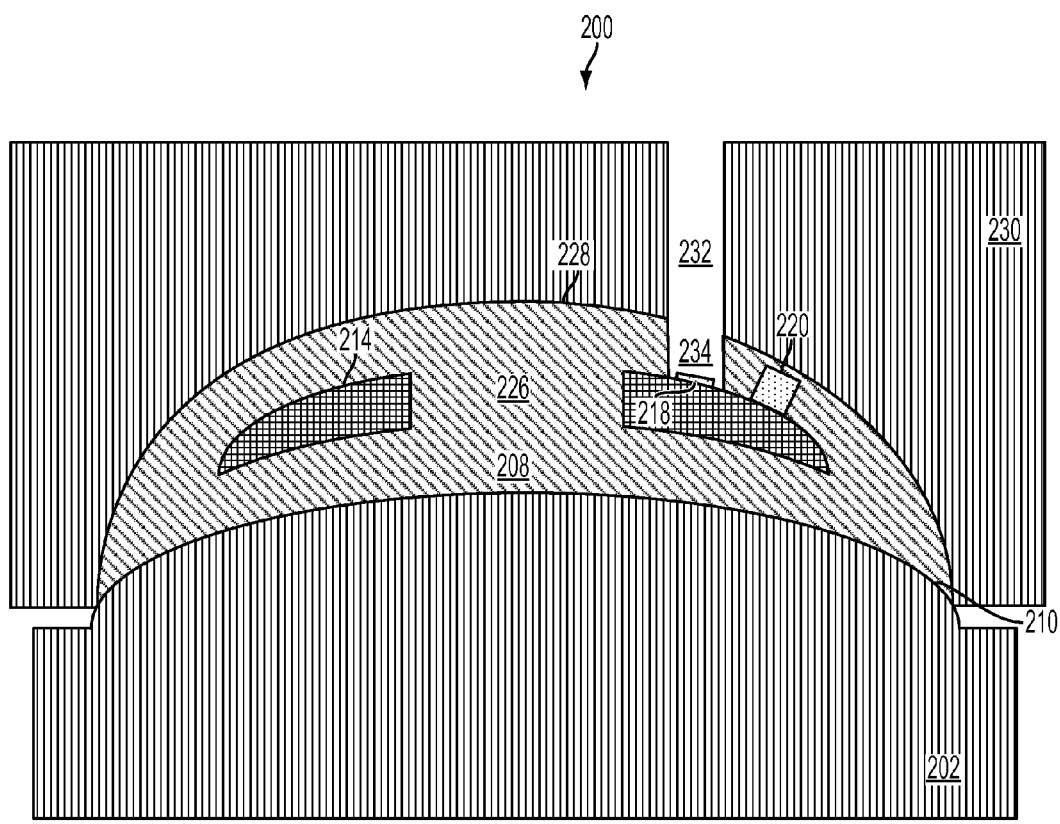
FIG. 2f is an illustration of formation of a channel, according to an example embodiment.

D. Forming a Channel Through the Second Polymer Layer Based on the Predetermined Rotational Orientation As mentioned above, at block 108, the fabrication device may form a channel through the second polymer layer based on the predetermined rotational orientation. FIGS. 2e and 2f illustrate example fabrication device 200 including example molding pieces that may be used to form the channel through the second polymer layer 226. In particular, FIG. 2e illustrates a fourth molding piece 230, which includes a molding channel 232. And FIG. 2f illustrates a channel 234 through the second polymer layer 226 based on the predetermined rotational orientation.

In order to form the channel 234, example fabrication device 200 may separate the first molding piece 202 from the third molding piece 222. When example fabrication device 200 separates the first molding piece 202 from the third molding piece 222, the first polymer layer 208 may stick to a side of the first molding piece 202. With this arrangement, the first molding piece 202 can hold the second polymer layer 226 and the first polymer layer 208 that together fully enclose the ring-shaped structure 214. In an example, the first polymer layer 208 and/or the first molding piece 202 can be surface treated, such that the first polymer layer 208 sticks to the side of the first molding piece 202. Additionally or alternatively, the third molding piece 222 and/or the second polymer layer 226 can be surface treated, such that the first polymer layer 208 sticks to the side of the first molding piece 202.

In order to form the channel 234, the fourth molding piece 230 may be placed over the first molding piece 202, which may hold the second polymer layer 226 and the first polymer layer 208 that fully enclose the ring-shaped structure 214. As shown in FIG. 2f, the fourth molding piece 230 encloses the second polymer layer 208.

In an example, the fourth molding piece 230 is placed over the first molding piece 202 based on the predetermined rotational orientation. With this arrangement, the molding channel 232 is located above the sensor 218. The fourth molding piece 230 may be placed over the first molding piece 202 based on the predetermined rotational orientation by any placement technique mentioned herein and/or any others known or later developed. In an example, the molding channel 232 can have at least one dimension based on one or more dimensions of the sensor 218.

After the fourth molding piece 230 is placed over the first molding piece 202, the channel 234 is formed through the second polymer layer 226 based on the predetermined rotational orientation. In an example, one or more dimensions of the channel 234 can be based on the predetermined rotational orientation and/or a thickness of the second polymer layer 226.

The channel 234 may be formed in various ways. In an example, the channel 234 can be formed by drilling the second polymer layer 226 through the molding channel 232. In this example or another example, one or more parameters of a drilling process to drill through the second polymer layer 226 through the molding channel 232 can be designed based on the predetermined rotational orientation and/or a thickness of the second polymer layer 226. Additionally or alternatively, one or more parameters of the drilling process to drill through the second polymer layer 226 through the molding channel 232 can be designed based on one or more dimensions of the sensor 218 and/or the electronics 220. As one example, one or more parameters of the drilling process to drill through the second polymer layer 226 can be designed based on the height of the electronics 220.

In another example, the channel 234 can be formed by removing material from the second polymer layer 226 by laser ablation. In this example or another example, one or more parameters of a laser ablation process to remove material from the second polymer layer 226 can be designed based on the predetermined rotational orientation and/or a thickness of the second polymer layer 226. Additionally or alternatively, one or more parameters of the laser ablation process to remove material from the second polymer layer 226 can be designed based on one or more dimensions of the sensor 218 and/or the electronics 220. As one example, one or more parameters of the laser ablation process to remove material from the second polymer layer 226 can be designed based on the height of the electronics 220.

In another example, the channel 234 can be formed by etching second polymer layer 226 through the molding channel 232. Various etching techniques may be used to etch the second polymer layer 226 through the molding channel 232 to form the channel 234. In an example, the second polymer layer 226 can be etched by an inductively coupled plasma, such as an oxygen plasma containing fluorine. In this example or another example, one or more parameters of an etching process to etch the second polymer layer 226 through the molding channel 232 can be designed based on the predetermined rotational orientation and/or a thickness of the second polymer layer 226. Additionally or alternatively, one or more parameters of the etching process to etch through the second polymer layer 226 through the molding channel 232 can be designed based on one or more dimensions of the sensor 218 and the electronics 220. As one example, one or more parameters of the etching process to etch through the second polymer layer 226 can be designed based on the height of the electronics 220.

In yet another example, the ring-shaped structure 214 may further comprise a metal film (not shown) over the sensor 218, such that the metal film acts as an etch stop. With this arrangement, the metal film may stay intact during an etching process to etch the second polymer layer 226 through the molding channel 232. Accordingly, example method 100 may further comprise removing the metal film. In an example, the metal film can be removed by etching the metal film, such as soaking each of the metal film, the first polymer layer 208, and the second polymer 226 in a metal etchant. With this arrangement, the metal etchant may not etch the first polymer layer 208 and/or the second polymer layer 226. Other techniques for removing the metal film are possible as well.

As mentioned above, FIG. 3 illustrates example eye-mountable device 300 fabricated according to an example embodiment. In particular, FIG. 3 illustrates an anterior side 306 including a channel 318.

In example eye-mountable device 300, a ring-shaped structure 308 is embedded in the transparent polymer 302. The ring-shaped structure 308 has an outer diameter 310 and an asymmetric inner diameter 312 and includes a sensor 314 configured to detect an analyte and electronics 316. In an example, the asymmetric inner diameter 312 can define a rotational orientation of the ring-shaped structure 308 relative to the channel 318, such that the sensor 314 is configured to receive the analyte through the channel 318. With this arrangement, the ring-shaped structure 308 is fully enclosed by the transparent polymer 302, except for the sensor 314 being exposed by the channel 318.

In some examples, one or more dimensions of the channel 318 may be based on one or more dimensions of the sensor 314 and/or the electronics 316. As one example, a width of the channel 318 can be based on a width of the sensor 314. As another example, a height of the channel 318 can be based on a height of the electronics 316.

E. Forming a Channel with a Mask Layer

The example methods described above involve a method of fabricating an eye-mountable device that involves forming a channel through a second polymer layer. In another example, a mask layer may be formed before forming the second polymer layer. Further, in such an example, after the second polymer is formed, the mask layer may be removed to form a channel.

Figure 4:
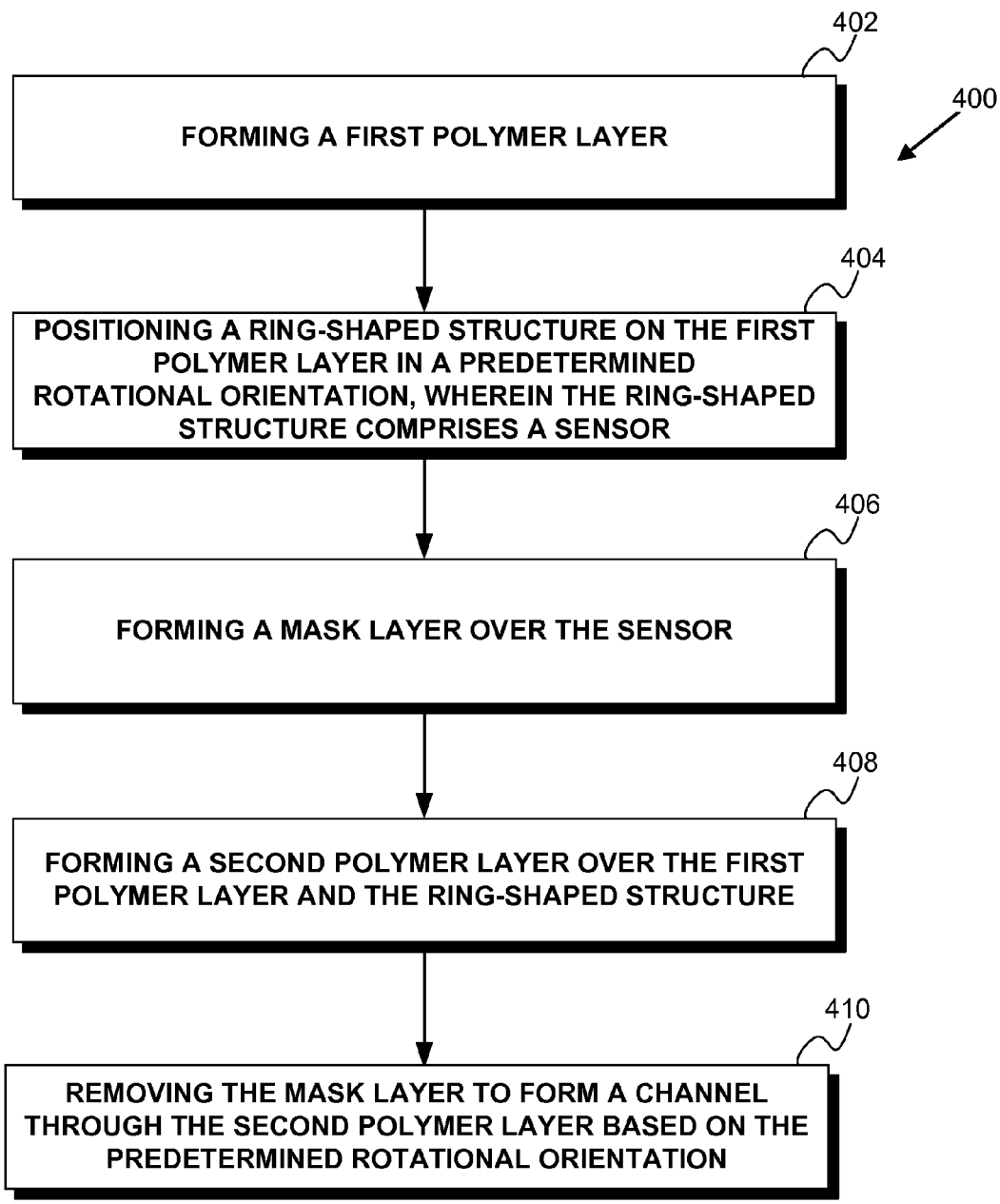
FIG. 4 is a flow chart illustrating another example method according to an example embodiment.

FIG. 4 is a flow chart illustrating a method according to an example embodiment. More specifically, example method 400 involves forming a first polymer layer, as shown by block 402. Example method 400 may then involve positioning a ring-shaped structure on the first polymer layer in a predetermined rotational orientation, wherein the ring-shaped structure comprises a sensor, as shown by block 404. Further, example method 400 may then involve forming a mask layer over the sensor, as shown by block 406. Further still, example method 400 may involve forming a second polymer layer over the first polymer layer and the ring-shaped structure, as shown by block 408. Example method 400 may then involve removing the mask layer to form a channel through the second polymer layer based on the predetermined rotational orientation, as shown by block 410.

For purposes of illustration, example method 400 is described below as being carried out by a fabrication device that utilizes cast or compression molding. It should be understood, however, that example method 400 may be carried out by a fabrication device that utilizes other methods for forming the polymer layers.

As mentioned above, at block 402, the fabrication device may be used to form a first polymer layer. Block 402 can be arranged like block 102. Further, the fabrication device can be arranged like example fabrication device 200 as illustrated in FIG. 2a.

As mentioned above, at block 404, a ring-shaped structure may be positioned on the first polymer layer in a predetermined rotational orientation. Block 404 can be arranged like block 104. Further, the ring-shaped structure can be positioned on the first polymer layer like the ring-shaped structure 214 is positioned on the first polymer layer 208 as illustrated in FIGS. 2b and 2c.

Figure 5A:
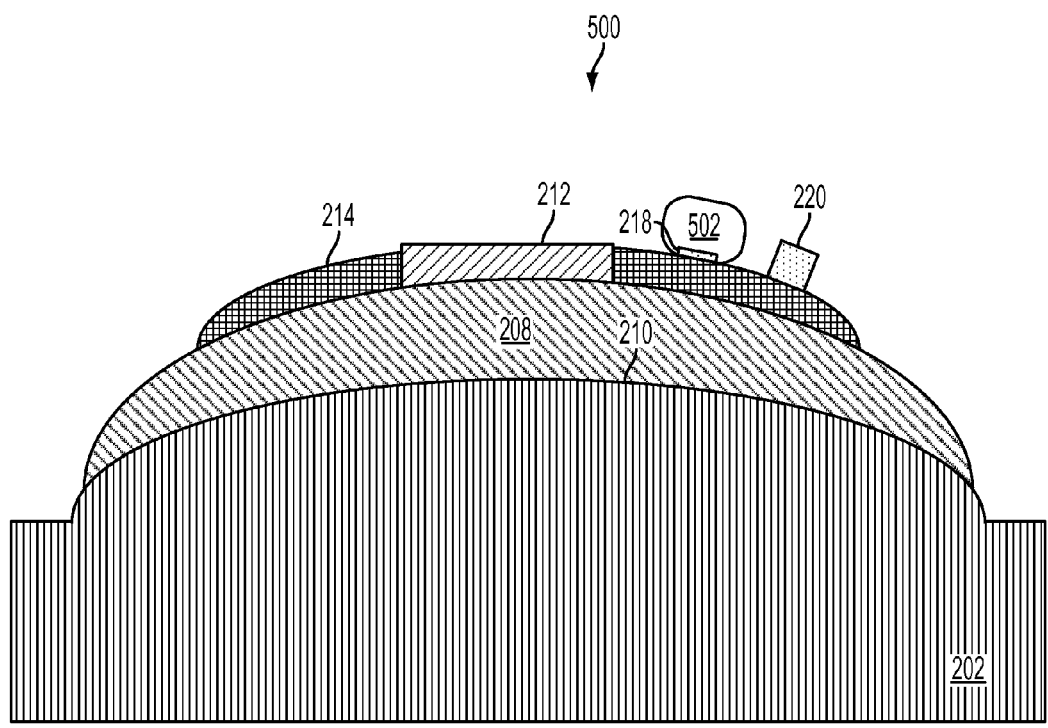
FIG. 5a is an illustration of formation of a mask layer, according to an example embodiment.

As mentioned above, at block 406, a mask layer may be formed over the sensor. FIG. 5a illustrates an example fabrication device 500 forming the mask layer over the sensor 218. In particular, FIG. 5a illustrates a mask layer 502. The mask layer 502 may be formed over the sensor 218 in a variety of ways. In an example, the mask layer 502 can be formed over the sensor 218 by placing one or more drops of a forming solution over the sensor 218. The forming solution may then be dried to form the mask layer 502.

In an example, the one or more drops of the forming solution can be placed over the sensor 218 based on the predetermined rotational orientation by the positioning apparatus described herein. Other techniques for placing the one or more drops of the forming solution over the sensor 218 based on the predetermined rotational orientation are possible as well.

In an example, the forming solution can comprise water and a water-soluble material, such as polyethylene glycol. Other forming solutions are possible as well.

In an example, a volume of the forming solution can be selected based on one or more dimensions of the sensor 218 and/or the electronics 220. As one example, the volume of the forming solution can be selected based on a width of the sensor 218. Additionally or alternatively, the volume of the forming solution can be selected based on the height of the electronics 220. With this arrangement, one or more dimensions of the mask layer 502 can be selected based on the one or more parameters of the sensor 218 and/or the electronics 220.

Figure 5B:
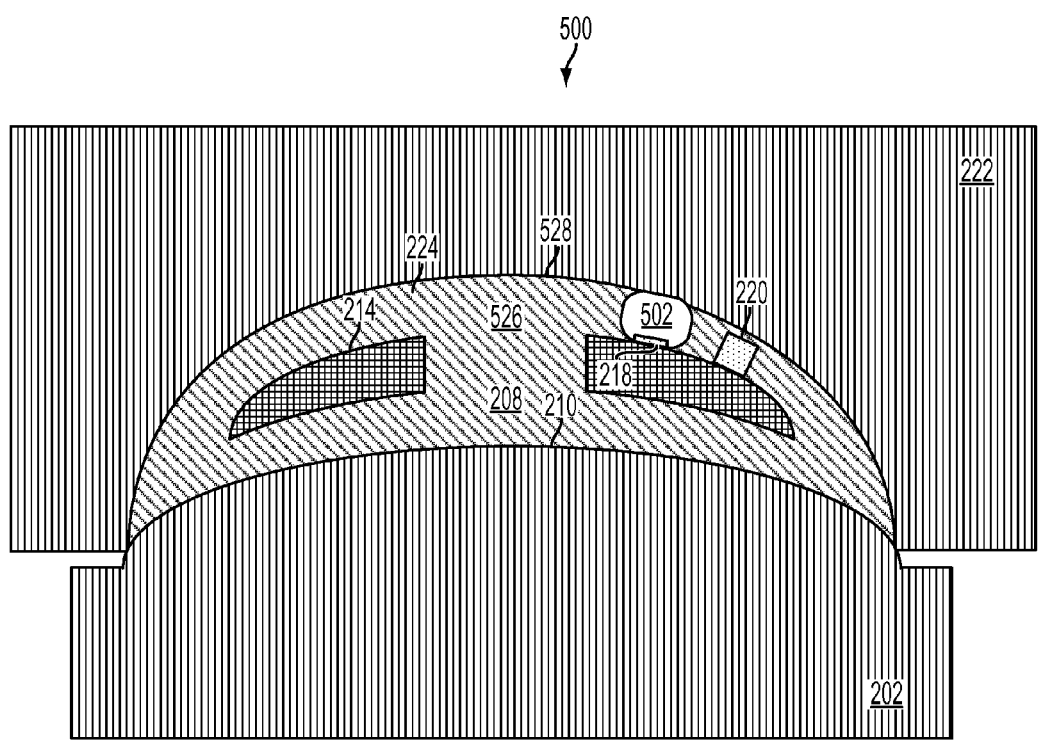
FIG. 5b is an illustration of formation of a second polymer layer, according to an example embodiment.

As mentioned above, at block 408, the fabrication device may form a second polymer layer over the first polymer and the ring-shaped structure. FIG. 5b illustrates example fabrication device 500 including example molding pieces that may be used to form the second polymer layer. In particular, FIG. 5b illustrates the third molding piece 222. The first molding piece 202 and the third molding piece 222 may define a second cavity.

The first molding piece 202, which already holds the first polymer layer 208 to which the ring-shaped structure 214 is mounted (as illustrated in FIG. 2c), may be filled with the polymer material 224. The polymer material 224 may be formed into a second polymer layer 526 by compression between the first molding piece 202 and the third molding piece 222. However, the mask layer 502 may block the second polymer layer 226 from molding over the sensor 218. As a result, the second polymer layer 226 may mold over the ring-shaped structure 214, such that the ring-shaped structure 214 is fully enclosed by the first polymer layer 208 and the second polymer layer 226 except for the sensor 218 being enclosed by the mask layer 502.

After the second polymer layer 526 is formed, example fabrication device 500 may cure the second polymer layer 526. In an example, the second polymer layer 526 can be cured like the second polymer layer 226. However, in other examples, the second polymer layer 526 may be cured by different techniques than the second polymer layer 226. The second polymer layer 526 can be cured by any of the techniques mentioned herein. In an example, example fabrication device 500 may cure the first polymer layer 208 at this stage.

After the second polymer layer 526 is cured, there may not be a visible boundary line separating the first polymer layer 208 from the second polymer layer 526. As mentioned above, FIG. 3 illustrates example eye-mountable device 300. In particular, FIG. 3 illustrates example eye-mountable device 300 includes the transparent polymer 302. The transparent polymer 302 can be arranged like the first polymer layer 208 and the second polymer layer 526.

Returning to FIG. 5b, example fabrication device 500 may further comprise one or more alignment pins (not shown), such as a plurality of dowel pins, for aligning the third molding piece 222 and the first molding piece 202. The one or more alignment pins can assist in forming the second polymer layer 526 by aligning the third molding piece 222 with the first molding piece 202.

The first molding piece 202 and the third molding piece 222 may be configured to achieve a given desired thickness of a layer formed between the two cavities. As one example, the first molding piece 202 and the third molding piece 222 may be designed so as to define a thickness of the second polymer layer 526. As another example, the first molding piece 202 and the third molding piece 222 may be designed so as to define a final thickness of an eye-mountable device, such as example eye-mountable device 300. In an example, the first molding piece 202 and the third molding piece 222 can be designed so as to allow for a layer having a given desired thickness between the two pieces (in addition to a thickness of the first polymer 208). As such, when the first molding piece 202 and the third molding piece 222 are pressed together during formation of a layer, the resulting layer will have the given desired thickness.

In an example, the second polymer layer 526 has a thickness of greater than 50 micrometers. However, in other examples, the second polymer layer 526 can have a thickness between 50 and 300 micrometers, such as 130 micrometers. It should be understood that since the second polymer layer 526 molds over the ring-shaped structure 214 except for the mask layer 502, the second polymer layer 526 may not have a uniform thickness. For instance, the thickness of the second polymer layer 526 above the electronics 220 may be less than the thickness of the second polymer layer 526 that is not touching the electronics 220.

In an example, the thickness of the second polymer layer 526 can be selected based on a particular analyte or analytes that the eye-mountable device, such as example eye-mountable device 300, is configured to detect. For example, an optimal thickness for a first analyte may be 10 micrometers, while an optimal thickness for a second analyte may be 25 micrometers. Other examples are possible as well.

In an example, the second polymer layer 526 can be composed of the same polymer material as first polymer layer 208 and/or second polymer layer 226. However, in other examples, the second polymer layer 526 can be composed of a different polymer material than the first polymer layer 208 and/or second polymer layer 226. The second polymer layer 526 can be any one of the polymer materials mentioned herein. In an example, the ring-shaped structure 214 can be more rigid than the second polymer layer 526.

The second polymer layer 526 defines an anterior side 528 of an eye-mountable device. That is, the second polymer layer 526 defines an outer edge of the eye-mountable device. When mounted on an eye of a user, the anterior side 528 of the eye-mountable device defined by the second polymer layer 526 corresponds to the side of the device that is not touching the eye of the user. The third molding piece 222 may be shaped so as to define a shape of the anterior side 528. For example, a curvature of the anterior side 528 may be defined by the third molding piece 222.

Figure 5C:
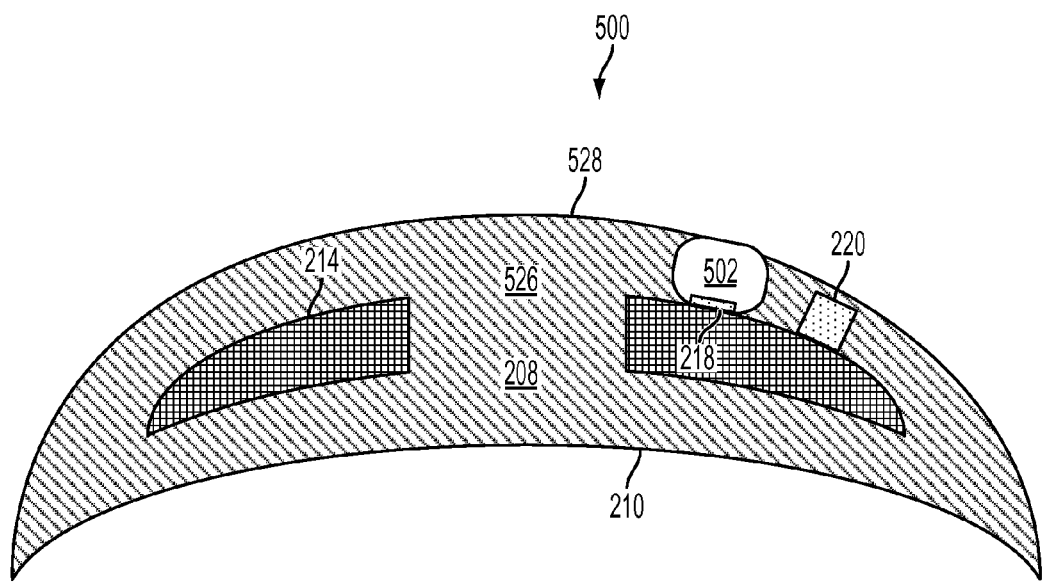
FIG. 5c is an illustration of removal of a mask layer, according to an example embodiment.
Figure 5D:
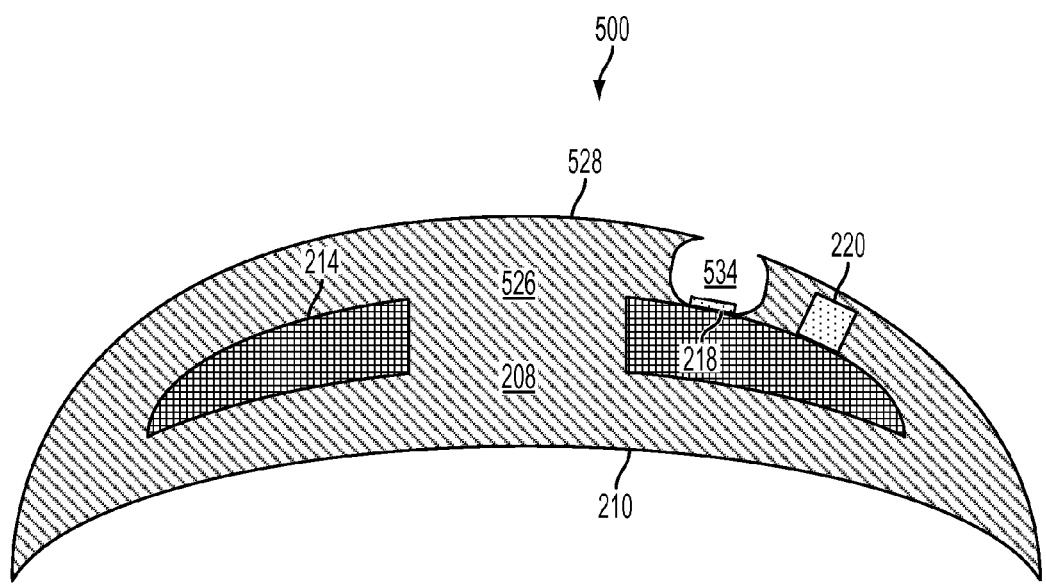
FIG. 5d is an illustration of formation of a channel, according to an example embodiment.

As mentioned above, at block 410, the mask layer is removed to form a channel through the second polymer layer based on the predetermined rotational orientation. FIGS. 5c and 5d illustrate example fabrication device 500 removing the mask layer. In particular, FIGS. 5c and 5d illustrate example fabrication device 500 removing the mask layer 502 to form a channel 534 through the second polymer layer 526.

In order to remove the mask layer 502 to form the channel 534, example fabrication device 500 may separate the first molding piece 202 from the third molding piece 222. When example fabrication device 500 separates the first molding piece 202 from the third molding piece 222, the first polymer layer 208 may stick to a side of the first molding piece 202. With this arrangement, the first molding piece 202 can hold the second polymer layer 226 and the first polymer layer 208 that together fully enclose the ring-shaped structure 214 except for the sensor 218 being enclosed by the mask layer 502. In an example, the first polymer layer 208 and/or the first molding piece 202 can be surface treated, such that the first polymer layer 208 sticks to the side of the first molding piece 202. Additionally or alternatively, the third molding piece 222 and/or the second polymer layer 526 can be surface treated, such that the first polymer layer 208 sticks to the side of the first molding piece 202.

After the first molding piece 202 is separated from the third molding piece 222, the first polymer layer 208 and the second polymer layer 526 that together fully enclose the ring-shaped structure 214 except for the sensor 218 being enclosed by the mask layer 502 are removed from the first molding piece 202. In an example, removing the first polymer layer 208 and second polymer layer 526 from the first mold piece can comprise removing the surface treatment of the first polymer layer 208 and/or the first molding piece 202.

After the first polymer layer 208 and the second polymer layer 526 are removed from the first molding piece 202, the mask layer 502 may then be removed to form the channel 534 through the second polymer layer 526, such that the sensor 218 is configured to receive the analyte via the channel. The channel 534 may have one or dimensions based on one or more dimensions of the mask layer 502. The channel 534 can be arranged like the channel 234 and/or the channel 318.

The mask layer 502 can be removed to form the channel 534 in a variety of ways. As one example, the mask layer 502 can be removed to form the channel 534 by dissolving the mask layer 502. In an example, the mask layer 502 can be dissolved by soaking each of the mask layer 502, the first polymer layer 508, and the second polymer layer 526 in a dissolving fluid that dissolves the mask layer 502. With this arrangement, the dissolving fluid may not dissolve the first polymer layer 208 and/or the second polymer layer 526. Other techniques for dissolving the mask layer 502 are possible as well.

In an example, the dissolving fluid can be selected based on the forming solution, the material of the first polymer layer 208 and/or the material of the second polymer layer 526. In an example, the dissolving fluid can be water. Other dissolving fluids are possible as well.

III. Example Systems and Devices

As mentioned above, an eye-mountable device may be fabricated using the example methods described above. Further, the eye-mountable device may be configured to monitor health-related information based on at least one analyte detected in a tear film of a user wearing the eye-mountable device. An example eye-mountable device configured to monitor health-related information based on at least one analyte detected from an eye of a user is described in greater detail below with reference to FIGS. 6 and 7a-d.

A sensor apparatus in accordance with an exemplary embodiment may include a sensor, control electronics and an antenna all situated on a substrate. The control electronics may operate the sensor to perform readings and operate the antenna to wirelessly communicate the readings from the sensor to an external reader via the antenna. The sensor can be arranged on the substrate to face outward, away from the corneal surface of the user, so as to generate clinically relevant readings from tear fluid of the user that the sensor receives via a channel in the anterior side of the eye-mountable device. For example, the sensor can be suspended in the lens material and situated such that the sensor is less than 10 micrometers from the anterior edge of the eye-mountable device. The sensor can generate an output signal indicative of a concentration of an analyte that the sensor receives via the channel.

Figure 6:
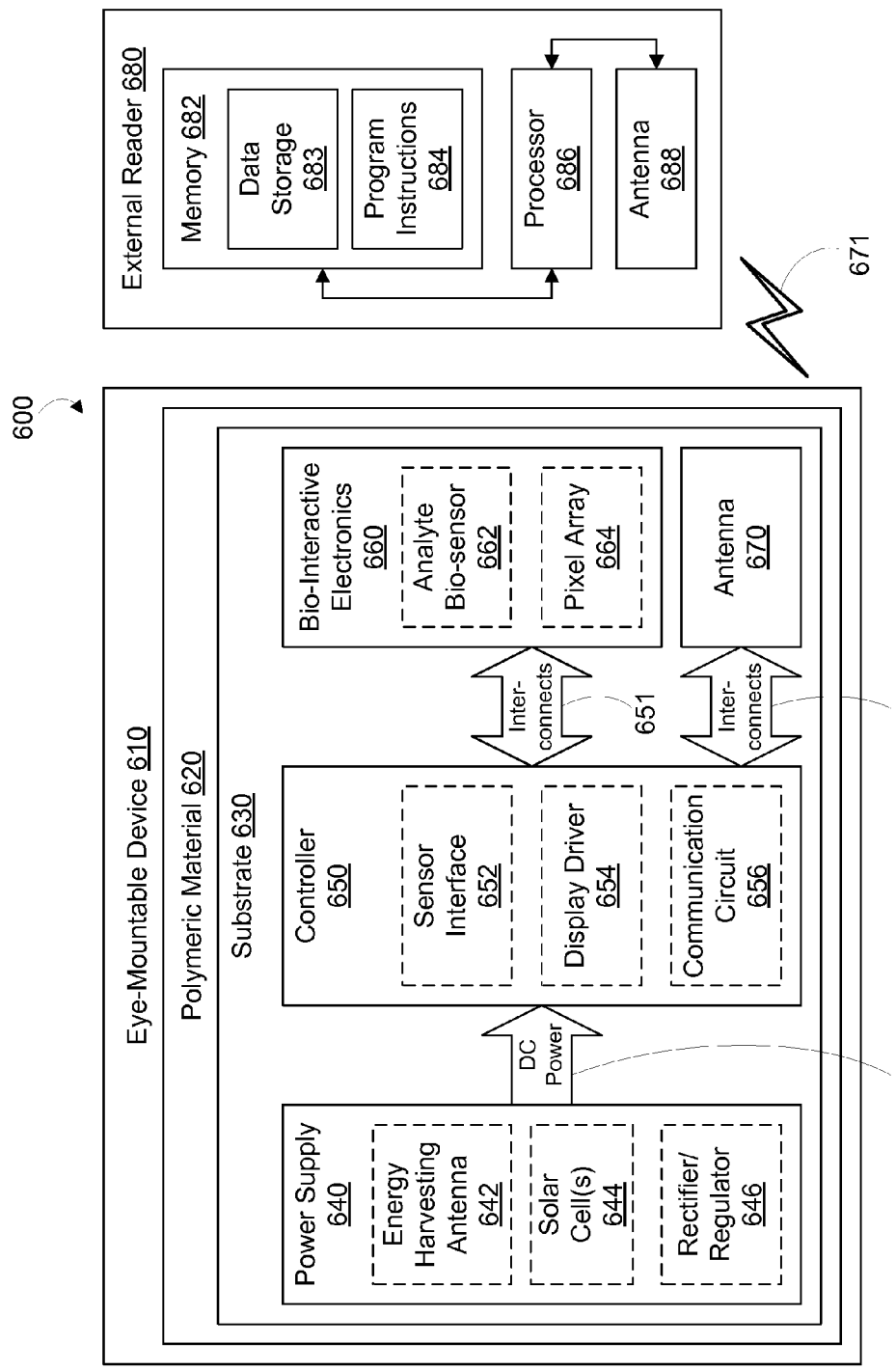
FIG. 6 is a block diagram of a system with an eye-mountable device in wireless communication with an external reader, according to an example embodiment.

FIG. 6 is a block diagram of a system 600 with an eye-mountable device 610 in wireless communication with an external reader 680. The exposed regions of the eye-mountable device 610 are made of a polymeric material 620 formed to be contact-mounted to a corneal surface of an eye. In accordance with the exemplary methods, polymeric material 620 may comprise a first polymer layer and a second polymer layer.

The sensor apparatus may comprise a substrate, such as substrate 630 that is embedded in the polymeric material 620 to provide a mounting surface for a power supply 640, a controller 650, bio-interactive electronics 660, and a communication antenna 670. The bio-interactive electronics 660 are operated by the controller 650. The power supply 640 supplies operating voltages to the controller 650 and/or the bio-interactive electronics 660. The antenna 670 is operated by the controller 650 to communicate information to and/or from the eye-mountable device 610. The antenna 670, the controller 650, the power supply 640, and the bio-interactive electronics 660 can all be situated on the embedded substrate 630. Because the eye-mountable device 610 includes electronics and is configured to be contact-mounted to an eye, it may also be referred to as an ophthalmic electronics platform.

To facilitate contact-mounting, the polymeric material 620 can have a concave surface configured to adhere ("mount") to a moistened corneal surface (e.g., by capillary forces with a tear film coating the corneal surface). Additionally or alternatively, the eye-mountable device 610 can be adhered by a vacuum force between the corneal surface and the polymeric material due to the concave curvature. While mounted with the concave surface against the eye, the anterior or outward-facing surface of the polymeric material 620 can have a convex curvature that is formed to not interfere with eye-lid motion while the eye-mountable device 610 is mounted to the eye. For example, the polymeric material 620 can be a substantially transparent curved polymeric disk shaped similarly to a contact lens.

The polymeric material 620 can include one or more biocompatible materials, such as those employed for use in contact lenses or other ophthalmic applications involving direct contact with the corneal surface. The polymeric material 620 can optionally be formed in part from such biocompatible materials or can include an outer coating with such biocompatible materials. The polymeric material 620 can include materials configured to moisturize the corneal surface, such as hydrogels and the like. In some instances, the polymeric material 620 can be a deformable ("non-rigid") material to enhance wearer comfort. In some instances, the polymeric material 620 can be shaped to provide a predetermined, vision-correcting optical power, such as can be provided by a contact lens.

The substrate 630 includes one or more surfaces suitable for mounting the bio-interactive electronics 660, the controller 650, the power supply 640, and the antenna 670. The substrate 630 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide) can be patterned on the substrate 630 to form circuitry, electrodes, etc. For example, the antenna 670 can be formed by depositing a pattern of gold or another conductive material on the substrate 630. Similarly, interconnects 651, 657 between the controller 650 and the bio-interactive electronics 660, and between the controller 650 and the antenna 670, respectively, can be formed by depositing suitable patterns of conductive materials on the substrate 630. A combination of resists, masks, and deposition techniques can be employed to pattern materials on the substrate 630.

The substrate 630 can be a relatively rigid polymeric material, such as polyethylene terephthalate ("PET"), paralyene or another material sufficient to structurally support the circuitry and/or electronics within the polymeric material 620. The eye-mountable device 610 can alternatively be arranged with a group of unconnected substrates rather than a single substrate. For example, the controller 650 and a bio-sensor or other bio-interactive electronic component can be mounted to one substrate, while the antenna 670 is mounted to another substrate and the two can be electrically connected via the interconnects 657.

In some embodiments, the bio-interactive electronics 660 (and the substrate 630) can be positioned away from the center of the eye-mountable device 610 and thereby avoid interference with light transmission to the eye through the center of the eye-mountable device 610. For example, where the eye-mountable device 610 is shaped as a concave-curved disk, the substrate 630 can be embedded around the periphery (e.g., near the outer circumference) of the disk. In some embodiments, the bio-interactive electronics 660 (and the substrate 630) can be positioned in the center region of the eye-mountable device 610. The bio-interactive electronics 660 and/or substrate 630 can be substantially transparent to incoming visible light to mitigate interference with light transmission to the eye. Moreover, in some embodiments, the bio-interactive electronics 660 can include a pixel array 664 that emits and/or transmits light to be perceived by the eye according to display driver instructions. Thus, the bio-interactive electronics 660 can optionally be positioned in the center of the eye-mountable device so as to generate perceivable visual cues to a wearer of the eye-mountable device 610, such as by displaying information via the pixel array 664.

The substrate 630 can be shaped as a flattened ring with a radial width dimension sufficient to provide a mounting platform for the embedded electronics components. The substrate 630 can have a thickness sufficiently small to allow the substrate 630 to be embedded in the polymeric material 620 without influencing the profile of the eye-mountable device 610. The substrate 630 can have a thickness sufficiently large to provide structural stability suitable for supporting the electronics mounted thereon. For example, the substrate 630 can be shaped as a ring with a diameter of about 10 millimeters, a radial width of about 1 millimeter (e.g., an outer radius 1 millimeter larger than an inner radius), and a thickness of about 50 micrometers. The substrate 630 can optionally be aligned with the curvature of the anterior side of the eye-mountable device.

The power supply 640 is configured to harvest ambient energy to power the controller 650 and bio-interactive electronics 660. For example, a radio-frequency energy-harvesting antenna 642 can capture energy from incident radio radiation. Additionally or alternatively, solar cell(s) 644 ("photovoltaic cells") can capture energy from incoming ultraviolet, visible, and/or infrared radiation. Furthermore, an inertial power scavenging system can be included to capture energy from ambient vibrations. The energy harvesting antenna 642 can optionally be a dual-purpose antenna that is also used to communicate information to the external reader 680. That is, the functions of the communication antenna 670 and the energy harvesting antenna 642 can be accomplished with the same physical antenna.

A rectifier/regulator 646 can be used to condition the captured energy to a stable DC supply voltage 641 that is supplied to the controller 650. For example, the energy harvesting antenna 642 can receive incident radio frequency radiation. Varying electrical signals on the leads of the antenna 642 are output to the rectifier/regulator 646. The rectifier/regulator 646 rectifies the varying electrical signals to a DC voltage and regulates the rectified DC voltage to a level suitable for operating the controller 650. Additionally or alternatively, output voltage from the solar cell(s) 644 can be regulated to a level suitable for operating the controller 650. The rectifier/regulator 646 can include one or more energy storage devices arranged to mitigate high frequency variations in the ambient energy gathering antenna 642 and/or solar cell(s) 644. For example, an energy storage device (e.g., capacitor, inductor, etc.) can be connected to the output of the rectifier 646 so as to function as a low-pass filter.

The controller 650 is turned on when the DC supply voltage 641 is provided to the controller 650, and the logic in the controller 650 operates the bio-interactive electronics 660 and the antenna 670. The controller 650 can include logic circuitry configured to operate the bio-interactive electronics 660 so as to interact with a biological environment of the eye-mountable device 610. The interaction could involve the use of one or more components, such as an analyte bio-sensor 662, in bio-interactive electronics 660 to obtain input from the biological environment. Alternatively or additionally, the interaction could involve the use of one or more components, such as the pixel array 664, to provide an output to the biological environment.

In one example, a sensor interface module 652 can be included for operating the analyte bio-sensor 662. The analyte bio-sensor 662 can be, for example, an amperometric electrochemical sensor that includes a working electrode and a reference electrode. Application of an appropriate voltage between the working and reference electrodes can cause an analyte to undergo electrochemical reactions (e.g., reduction and/or oxidation reactions) at the working electrode to generate an amperometric current. The amperometric current can be dependent on the analyte concentration, and thus the amount of amperometric current can provide an indication of analyte concentration. In some embodiments, the sensor interface module 652 can be a potentiostat configured to apply a voltage difference between the working and reference electrodes while measuring a current through the working electrode.

In some instances, a reagent can also be included to sensitize the electrochemical sensor to desired analytes. For example, a layer of glucose oxidase ("GOD") can be situated around the working electrode to catalyze glucose into hydrogen peroxide ($H_2O_2$). The hydrogen peroxide can then be oxidized at the working electrode, which releases electrons to the working electrode, which generates a current.

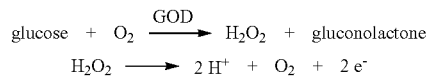

The current generated by either reduction or oxidation reactions can be approximately proportionate to the reaction rate. Further, the reaction rate can be dependent on the rate of analyte molecules reaching the electrochemical sensor electrodes to fuel the reduction or oxidation reactions, either directly or catalytically through a reagent. In a steady state, where analyte molecules diffuse to the electrochemical sensor electrodes from a sampled region at approximately the same rate that additional analyte molecules diffuse to the sampled region from surrounding regions, the reaction rate can be approximately proportionate to the concentration of the analyte molecules. The current can thus provide an indication of the analyte concentration.

The controller 650 can optionally include a display driver module 654 for operating a pixel array 664. The pixel array 664 can be an array of separately programmable light transmitting, light reflecting, and/or light emitting pixels arranged in rows and columns. The individual pixel circuits can optionally include liquid crystal technologies, microelectromechanical technologies, emissive diode technologies, etc. to selectively transmit, reflect, and/or emit light according to information from the display driver module 654. Such a pixel array 664 can also optionally include more than one color of pixels (e.g., red, green, and blue pixels) to render visual content in color. The display driver module 654 can include, for example, one or more data lines providing programming information to the separately programmed pixels in the pixel array 664 and one or more addressing lines for setting groups of pixels to receive such programming information. Such a pixel array 664 situated on the eye can also include one or more lenses to direct light from the pixel array to a focal plane perceivable by the eye.

The controller 650 can also include a communication circuit 656 for sending and/or receiving information via the antenna 670. The communication circuit 656 can optionally include one or more oscillators, mixers, frequency injectors, etc. to modulate and/or demodulate information on a carrier frequency to be transmitted and/or received by the antenna 670. In some examples, the eye-mountable device 610 is configured to indicate an output from a bio-sensor by modulating an impedance of the antenna 670 in a manner that is perceivable by the external reader 680. For example, the communication circuit 656 can cause variations in the amplitude, phase, and/or frequency of backscatter radiation from the antenna 670, and such variations can be detected by the external reader 680.

The controller 650 is connected to the bio-interactive electronics 660 via interconnects 651. For example, where the controller 650 includes logic elements implemented in an integrated circuit to form the sensor interface module 652 and/or display driver module 654, a patterned conductive material (e.g., gold, platinum, palladium, titanium, copper, aluminum, silver, metals, combinations of these, etc.) can connect a terminal on the chip to the bio-interactive electronics 660. Similarly, the controller 650 is connected to the antenna 670 via interconnects 657.

It is noted that the block diagram shown in FIG. 6 is described in connection with functional modules for convenience in description. However, embodiments of the eye-mountable device 610 can be arranged with one or more of the functional modules ("sub-systems") implemented in a single chip, integrated circuit, and/or physical feature. For example, while the rectifier/regulator 646 is illustrated in the power supply block 640, the rectifier/regulator 646 can be implemented in a chip that also includes the logic elements of the controller 650 and/or other features of the embedded electronics in the eye-mountable device 610. Thus, the DC supply voltage 641 that is provided to the controller 650 from the power supply 640 can be a supply voltage that is provided on a chip by rectifier and/or regulator components the same chip. That is, the functional blocks in FIG. 6 shown as the power supply block 640 and controller block 650 need not be implemented as separated modules. Moreover, one or more of the functional modules described in FIG. 6 can be implemented by separately packaged chips electrically connected to one another.

Additionally or alternatively, the energy harvesting antenna 642 and the communication antenna 670 can be implemented with the same physical antenna. For example, a loop antenna can both harvest incident radiation for power generation and communicate information via backscatter radiation.

The external reader 680 includes an antenna 688 (or group of more than one antennae) to send and receive wireless signals 671 to and from the eye-mountable device 610. The external reader 680 also includes a computing system with a processor 686 in communication with a memory 682. The memory 682 is a non-transitory computer-readable medium that can include, without limitation, magnetic disks, optical disks, organic memory, and/or any other volatile (e.g., RAM) or non-volatile (e.g., ROM) storage system readable by the processor 686. The memory 682 can include a data storage 683 to store indications of data structures, such as sensor readings (e.g., from the analyte bio-sensor 662), program settings (e.g., to adjust behavior of the eye-mountable device and/or external reader 680), etc. The memory can also include program instructions 684 for execution by the processor 686 to cause the external reader to perform processes specified by the program instructions 684. For example, the program instructions 684 can cause external reader 680 to provide a user interface that allows for retrieving information communicated from the eye-mountable device 610 (e.g., sensor outputs from the analyte bio-sensor 662). The external reader 680 can also include one or more hardware components for operating the antenna 688 to send and receive the wireless signals 671 to and from the eye-mountable device 610. For example, oscillators, frequency injectors, encoders, decoders, amplifiers, filters, etc. can drive the antenna 688 according to instructions from the processor 686.

The external reader 680 can be a smart phone, digital assistant, or other portable computing device with wireless connectivity sufficient to provide the wireless communication link 671. The external reader 680 can also be implemented as an antenna module that can be plugged in to a portable computing device, such as in an example where the communication link 671 operates at carrier frequencies not commonly employed in portable computing devices. In some instances, the external reader 680 is a special-purpose device configured to be worn relatively near a wearer's eye to allow the wireless communication link 671 to operate with a low power budget. For example, the external reader 680 can be integrated in a piece of jewelry such as a necklace, earring, etc. or integrated in an article of clothing worn near the head, such as a hat, headband, etc.

In an example where the eye-mountable device 610 includes an analyte bio-sensor 662, the system 600 can be operated to monitor the analyte concentration in tear film on the surface of the eye. Thus, the eye-mountable device 610 can be configured as a platform for an ophthalmic analyte bio-sensor. The tear film is an aqueous layer secreted from the lacrimal gland to coat the eye. The tear film is in contact with the blood supply through capillaries in the structure of the eye and includes many biomarkers found in blood that are analyzed to characterize a person's health condition(s). For example, the tear film includes glucose, calcium, sodium, cholesterol, potassium, other biomarkers, etc. The biomarker concentrations in the tear film can be systematically different than the corresponding concentrations of the biomarkers in the blood, but a relationship between the two concentration levels can be established to map tear film biomarker concentration values to blood concentration levels. For example, the tear film concentration of glucose can be established (e.g., empirically determined) to be approximately one tenth the corresponding blood glucose concentration. Thus, measuring tear film analyte concentration levels provides a non-invasive technique for monitoring biomarker levels in comparison to blood sampling techniques performed by lancing a volume of blood to be analyzed outside a person's body. Moreover, the ophthalmic analyte bio-sensor platform disclosed here can be operated substantially continuously to enable real time monitoring of analyte concentrations.

To perform a reading with the system 600 configured as a tear film analyte monitor, the external reader 680 can emit radio frequency radiation 671 that is harvested to power the eye-mountable device 610 via the power supply 640. Radio frequency electrical signals captured by the energy harvesting antenna 642 (and/or the communication antenna 670) are rectified and/or regulated in the rectifier/regulator 646 and a regulated DC supply voltage 647 is provided to the controller 650. The radio frequency radiation 671 thus turns on the electronic components within the eye-mountable device 610. Once turned on, the controller 650 operates the analyte bio-sensor 662 to measure an analyte concentration level. For example, the sensor interface module 652 can apply a voltage between a working electrode and a reference electrode in the analyte bio-sensor 662 sufficient to cause the analyte to undergo an electrochemical reaction at the working electrode. The current through the working electrode can be measured to provide the sensor output indicative of the analyte concentration. The controller 650 can operate the antenna 670 to communicate the sensor results back to the external reader 680 (e.g., via the communication circuit 656). The sensor result can be communicated by, for example, modulating an impedance of the antenna 670 such that the modulation in impedance is detected by the external reader 680. The modulation in antenna impedance can be detected by, for example, backscatter radiation from the antenna 670.

In some embodiments, the system 600 can operate to non-continuously ("intermittently") supply energy to the eye-mountable device 610 to power the on-board controller 650 and electronics 660. For example, radio frequency radiation 671 can be supplied to power the eye-mountable device 610 long enough to carry out a tear film analyte concentration measurement and communicate the results. For example, the supplied radio frequency radiation can provide sufficient power to charge two electrodes to a potential sufficient to induce electrochemical reactions, measure the resulting amperometric current, and modulate the antenna impedance to adjust the backscatter radiation in a manner indicative of the measured current. In such an example, the supplied radio frequency radiation 671 can be considered an interrogation signal from the external reader 680 to the eye-mountable device 610 to request a measurement. By periodically interrogating the eye-mountable device 610 (e.g., by supplying radio frequency radiation 671 to temporarily turn the device on) and storing the sensor results (e.g., via the data storage 683), the external reader 680 can accumulate a set of analyte concentration measurements over time without continuously powering the eye-mountable device 610.

Figure 7A:
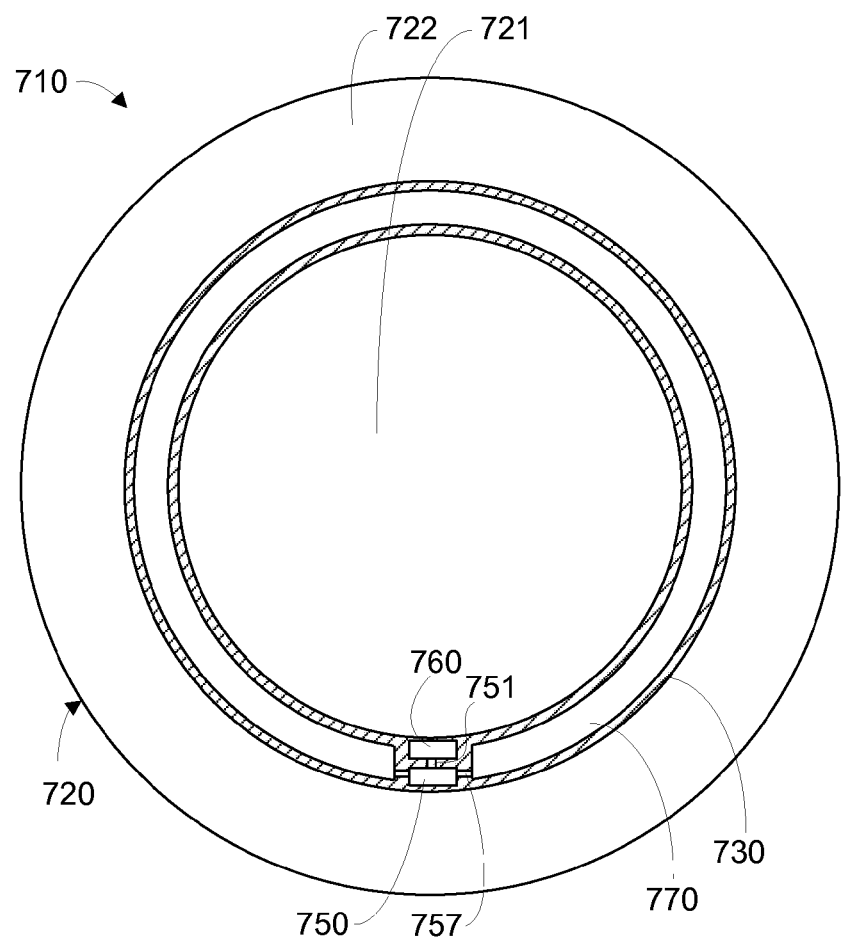
FIG. 7a is a top view of an example eye-mountable device, according to an example embodiment.
Figure 7B:
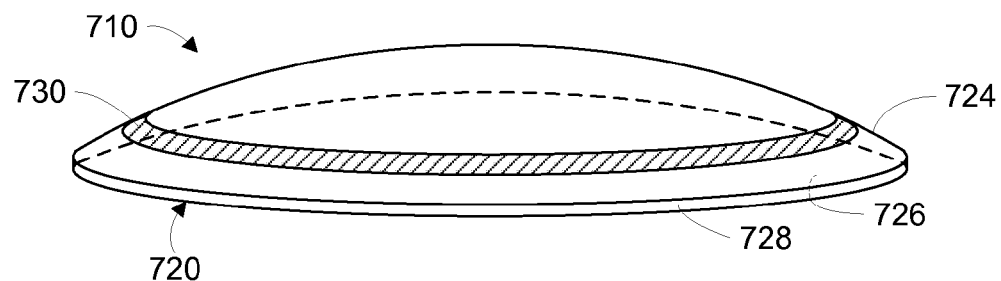
FIG. 7b is a side view of an example eye-mountable device, according to an example embodiment.

FIG. 7a is a top view of an example eye-mountable electronic device 710. FIG. 7b is a side view of the example eye-mountable electronic device shown in FIG. 7a. It is noted that relative dimensions in FIGS. 7a and 7b are not necessarily to scale, but have been rendered for purposes of explanation only in describing the arrangement of the example eye-mountable electronic device 710. Example eye-mountable device 710 is formed of a polymeric material 720 shaped as a curved disk. The polymeric material 720 can be a substantially transparent material to allow incident light to be transmitted to the eye while example eye-mountable device 710 is mounted to the eye. The polymeric material 720 can be a biocompatible material similar to those employed to form vision correction and/or cosmetic contact lenses in optometry, such as polyethylene terephthalate ("PET"), polymethyl methacrylate ("PMMA"), silicone hydrogels, combinations of these, etc. The polymeric material 720 can be formed with one side having a concave surface 726 suitable to fit over a corneal surface of an eye. The opposing side of the disk can have a convex surface 724 that does not interfere with eyelid motion while example eye-mountable device 710 is mounted to the eye. A circular outer side edge 728 connects the concave surface 724 and convex surface 726.

Example eye-mountable device 710 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of example eye-mountable device 710 can be selected according to the size and/or shape of the corneal surface of the wearer's eye.

While example eye-mountable device 710 is mounted in an eye, the convex surface 724 (i.e., the anterior surface) faces outward to the ambient environment while the concave surface 726 (i.e., the posterior surface) faces inward, toward the corneal surface. The convex surface 724 can therefore be considered an outer, top surface of example eye-mountable device 710 whereas the concave surface 726 can be considered an inner, bottom surface. The "top" view shown in FIG. 7a is facing the convex surface 724.

A substrate 730 is embedded in the polymeric material 720. The substrate 730 can be embedded to be situated along the outer periphery 722 of the polymeric material 720, away from the center region 721. The substrate 730 does not interfere with vision because it is too close to the eye to be in focus and is positioned away from the center region 721 where incident light is transmitted to the eye-sensing portions of the eye. Moreover, the substrate 730 can be formed of a transparent material to further mitigate any effects on visual perception.

The substrate 730 can be shaped as a flat, circular ring (e.g., a disk with a central hole). The flat surface of the substrate 730 (e.g., along the radial width) is a platform for mounting electronics such as chips (e.g., via flip-chip mounting) and for patterning conductive materials (e.g., via deposition techniques) to form electrodes, antenna(e), and/or connections. The substrate 730 and the polymeric material 720 can be approximately cylindrically symmetric about a common central axis. The substrate 730 can have, for example, a diameter of about 10 millimeters, a radial width of about 1 millimeter (e.g., an outer radius 1 millimeter greater than an inner radius), and a thickness of about 50 micrometers. However, these dimensions are provided for example purposes only. The substrate 730 can be implemented in a variety of different form factors.

A loop antenna 770, controller 750, and bio-interactive electronics 760 are disposed on the embedded substrate 730. The controller 750 can be a chip including logic elements configured to operate the bio-interactive electronics 760 and the loop antenna 770. The controller 750 is electrically connected to the loop antenna 770 by interconnects 757 also situated on the substrate 730. Similarly, the controller 750 is electrically connected to the bio-interactive electronics 760 by an interconnect 751. The interconnects 751, 757, the loop antenna 770, and any conductive electrodes (e.g., for an electrochemical analyte bio-sensor, etc.) can be formed from conductive materials patterned on the substrate 730 by a process for precisely patterning such materials, such as deposition or lithography. The conductive materials patterned on the substrate 730 can be, for example, gold, platinum, palladium, titanium, carbon, aluminum, copper, silver, silver-chloride, and/or other materials.

Figure 7D:
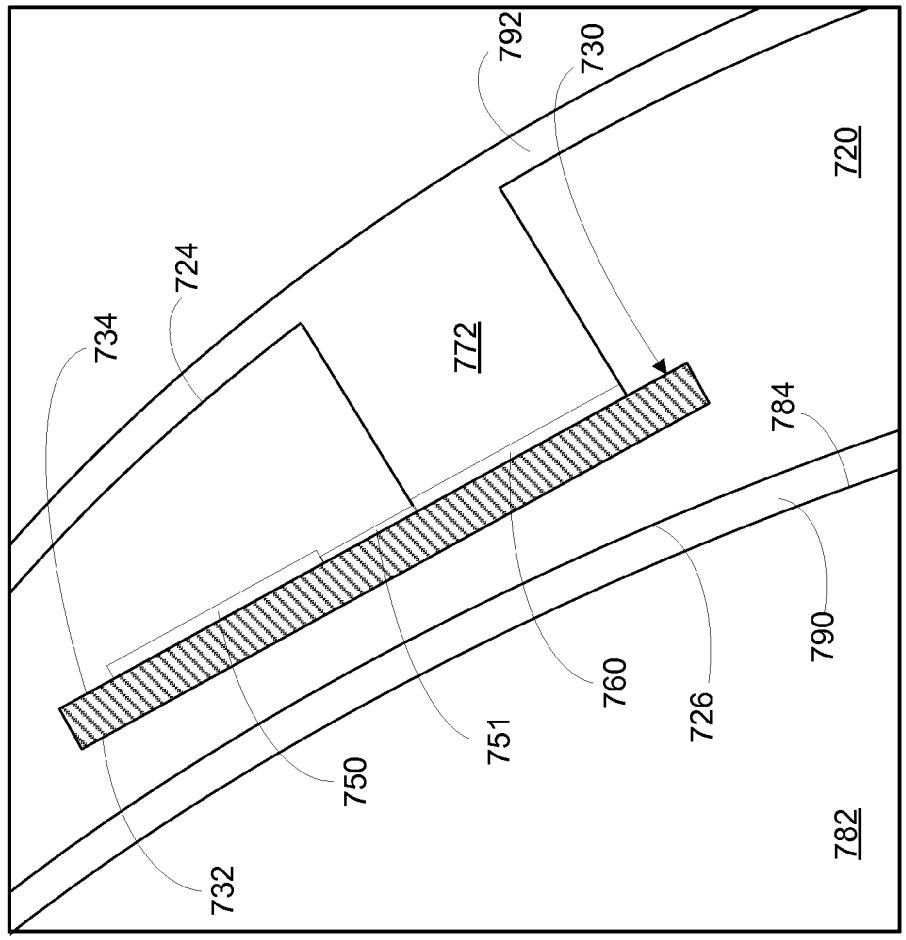
FIG. 7d is a side cross-section view showing the tear film layers surrounding the surfaces of the example eye-mountable device mounted as shown in FIG. 7c, according to an example embodiment.
Figure 7C:
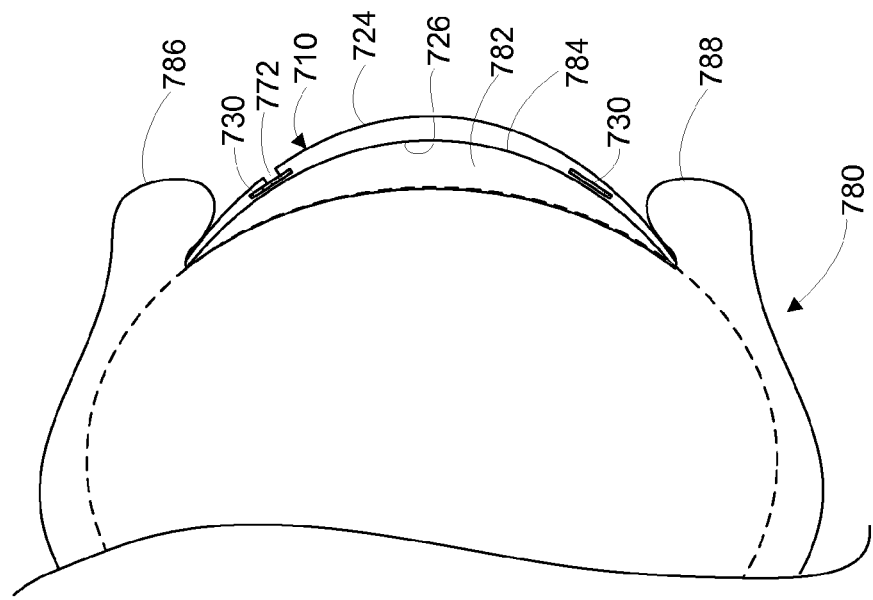
FIG. 7c is a side cross-section view of the example eye-mountable device of FIGS. 5a and 5b while mounted to a corneal surface of an eye, according to an example embodiment.

With reference to FIG. 7a, which is a view facing the convex surface 724 of example eye-mountable device 710, the bio-interactive electronics 760 is mounted to a side of the substrate 730 facing the convex surface 724. Where the bio-interactive electronics 760 includes an analyte bio-sensor, for example, mounting such a bio-sensor on the substrate 730 facing the convex surface 724 allows the bio-sensor to receive analyte concentrations in tear film through a channel 772 in the polymeric material 720 to the convex surface 724 (as shown in FIGS. 7c and 7d). In some embodiments, some electronic components can be mounted on one side of the substrate 530, while other electronic components are mounted to the opposing side, and connections between the two can be made through conductive materials passing through the substrate 730.

The loop antenna 770 is a layer of conductive material patterned along the flat surface of the substrate to form a flat conductive ring. In some instances, the loop antenna 770 can be formed without making a complete loop. For instance, the loop antenna can have a cutout to allow room for the controller 750 and bio-interactive electronics 760, as illustrated in FIG. 7a. However, the loop antenna 770 can also be arranged as a continuous strip of conductive material that wraps entirely around the flat surface of the substrate 730 one or more times. For example, a strip of conductive material with multiple windings can be patterned on the side of the substrate 730 opposite the controller 750 and bio-interactive electronics 760. Interconnects between the ends of such a wound antenna (e.g., the antenna leads) can be passed through the substrate 730 to the controller 750.

FIG. 7c is a side cross-section view of the example eye-mountable electronic device 710 while mounted to a corneal surface 784 of an eye 780. FIG. 7d is a close-in side cross-section view enhanced to show tear film layers 790, 792 surrounding the exposed surfaces 724, 726 of example eye-mountable device 710. It is noted that relative dimensions in FIGS. 7c and 7d are not necessarily to scale, but have been rendered for purposes of explanation only in describing the arrangement of example eye-mountable electronic device 710. For example, the total thickness of example eye-mountable device 710 can be about 200 micrometers, while the thickness of the tear film layers 790, 792 can each be about 10 micrometers, although this ratio is may not be reflected in the drawings. Some aspects are exaggerated to allow for illustration and facilitate explanation.

The eye 780 includes a cornea 782 that is covered by bringing the upper eyelid 786 and lower eyelid 788 together over the top of the eye 780. Incident light is received by the eye 780 through the cornea 782, where light is optically directed to light sensing elements of the eye 780 (e.g., rods and cones, etc.) to stimulate visual perception. The motion of the eyelids 786, 788 distributes a tear film across the exposed corneal surface 784 of the eye 780. The tear film is an aqueous solution secreted by the lacrimal gland to protect and lubricate the eye 780. When example eye-mountable device 710 is mounted in the eye 780, the tear film coats both the convex and concave surfaces 724, 726 with an inner layer 790 (along the concave surface 726) and an outer layer 792 (along the convex layer 724). The tear film layers 790, 792 can be about 10 micrometers in thickness and together account for about 10 microliters.

The tear film layers 790, 792 are distributed across the corneal surface 784 and/or the convex surface 724 by motion of the eyelids 786, 788. For example, the eyelids 786, 788 raise and lower, respectively, to spread a small volume of tear film across the corneal surface 784 and/or the convex surface 724 of example eye-mountable device 710. The tear film layer 790 on the corneal surface 784 also facilitates mounting example eye-mountable device 710 by capillary forces between the concave surface 726 and the corneal surface 784. In some embodiments, example eye-mountable device 710 can also be held over the eye in part by vacuum forces against the corneal surface 784 due to the concave curvature of the eye-facing concave surface 726.

As shown in the cross-sectional views in FIGS. 7c and 7d, the substrate 730 can be inclined such that the flat mounting surfaces of the substrate 730 are approximately parallel to the adjacent portion of the convex surface 724. As described above, the substrate 730 is a flattened ring with an inward-facing surface 732 (facing the concave surface 726 of the polymeric material 720) and an outward-facing surface 734 (facing the convex surface 724). The substrate 730 can have electronic components and/or patterned conductive materials mounted to either or both mounting surfaces 732, 734.

As shown in FIG. 7d, the bio-interactive electronics 760, the controller 750, and the conductive interconnect 751 are mounted on the outward-facing surface 734 such that the bio-interactive electronics 760 are facing the convex surface 724. As described above, the polymer layer defining the anterior side may be greater than 50 micrometers thick, whereas the polymer layer defining the posterior side may be less than 150 micrometers. Thus, the bio-interactive electronics 760 may be at least 50 micrometers away from the convex surface 724 and may be a greater distance away from the concave surface 726. However, in other examples, the bio-interactive electronics 760 may be mounted on the inward-facing surface 732 of the substrate 730 such that the bio-interactive electronics 760 are facing the concave surface 726. The bio-interactive electronics 760 could also be positioned closer to the concave surface 726 than the convex surface 724. With this arrangement, the bio-interactive electronics 760 can receive analyte concentrations in the tear film 792 through the channel 772.

IV. Conclusion

It should be understood that arrangements described herein are for purposes of example only. As such, those skilled in the art will appreciate that other arrangements and other elements (e.g., machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

The invention claimed is:

1. A method comprising:
   forming a first polymer layer, wherein the first polymer layer defines a posterior side of an eye-mountable device;
   positioning a ring-shaped structure on the first polymer layer in a predetermined rotational orientation, wherein the ring-shaped structure comprises a sensor configured to detect an analyte;
   forming a second polymer layer over the first polymer layer and the ring-shaped structure, such that the ring-shaped structure is fully enclosed by the first polymer layer and the second polymer layer, wherein the second polymer layer defines an anterior side of the eye-mountable device; and
   forming a channel through the second polymer layer based on the predetermined rotational orientation, such that the sensor is configured to receive the analyte via the channel.

2. The method of claim 1, wherein the first polymer layer has a thickness of less than 150 micrometers.

3. The method of claim 1, wherein the forming a first polymer layer comprises forming the first polymer layer in a molding piece.

4. The method of claim 1, wherein the ring-shaped structure is more rigid than the first and second polymer layers.

5. The method of claim 1, wherein the ring-shaped structure has a maximum height between 50 and 150 micrometers.

6. The method of claim 1, wherein the positioning a ring-shaped structure on the first polymer layer in a predetermined rotational orientation comprises placing an adhesive on the ring-shaped structure or the first polymer layer, such that the ring-shaped structure adheres to the first polymer layer.

7. The method of claim 1, wherein the second polymer layer has a thickness of greater than 50 micrometers.

8. The method of claim 1, wherein the forming a second polymer layer over the first polymer layer and the ring-shaped structure comprises forming the second polymer layer in a molding piece.

9. The method of claim 1, wherein the first polymer layer further comprises an alignment feature, and wherein the positioning a ring-shaped structure on the first polymer layer in a predetermined rotational orientation comprises aligning the ring-shaped structure with the alignment feature.

10. The method of claim 9, wherein the alignment feature comprises an asymmetric peg.

11. The method of claim 10, wherein the ring-shaped structure comprises a hole having an inner diameter configured to receive the asymmetric peg.

12. The method of claim 1, wherein the forming a channel through the second polymer layer comprises etching the second polymer layer.

13. The method of claim 12, wherein the ring-shaped structure further comprises a metal film over the sensor, such that the metal film acts as an etch stop.

14. The method of claim 12, wherein the etching the second polymer layer comprises etching the second polymer layer with an inductively coupled plasma.

15. The method of claim 14, wherein the inductively coupled plasma comprises oxygen plasma containing fluorine.

16. A method comprising:
    forming a first polymer layer, wherein the first polymer layer defines a posterior side of an eye-mountable device;
    positioning a ring-shaped structure on the first polymer layer in a predetermined rotational orientation, wherein the ring-shaped structure comprises a sensor configured to detect an analyte;
    forming a mask layer over the sensor, such that the sensor is enclosed by the mask layer;
    forming a second polymer layer over the first polymer layer and the ring-shaped structure, such that the ring-shaped structure is fully enclosed by the first polymer layer, the second polymer layer, and the mask layer, wherein the second polymer layer defines an anterior side of the eye-mountable device; and
    removing the mask layer to form a channel through the second polymer layer, such that the sensor is configured to receive the analyte via the channel.

17. The method of claim 16, wherein the removing the mask layer to form a channel in the second polymer layer comprises dissolving the mask layer.

18. The method of claim 17, wherein the dissolving the mask layer comprises soaking each of the mask layer, the first polymer layer, and the second polymer layer in water.

\* \* \* \* \*